(12) United States Patent
Davis et al.

(10) Patent No.: US 6,432,662 B1
(45) Date of Patent: Aug. 13, 2002

(54) ASSAY OF PEROXIDASE ACTIVITY

(75) Inventors: Paul D. Davis, Dublin, OH (US); Kelli D. Feather-Henigan, Rockford; Kimberly Hines, Crystal Lake, both of IL (US)

(73) Assignee: Pierce Chemical Company, Rockford, IL (US)

( * ) Notice: Subject to any disclaimer, the term of this patent is extended or adjusted under 35 U.S.C. 154(b) by 0 days.

(21) Appl. No.: 09/171,334

(22) PCT Filed: Apr. 15, 1997

(86) PCT No.: PCT/US97/06422

§ 371 (c)(1), (2), (4) Date: May 20, 1999

(87) PCT Pub. No.: WO97/39142

PCT Pub. Date: Oct. 23, 1997

(51) Int. Cl.[7] .................................................. C12Q 1/28

(52) U.S. Cl. ................................. 435/28; 435/8; 435/27

(58) Field of Search ................................ 435/8, 27, 28, 435/968; 546/334

(56) References Cited

U.S. PATENT DOCUMENTS 5,171,668 A * 12/1992 Sugiyama .................... 435/28
5,616,719 A * 4/1997 Davalian et al. ............ 546/334
5,709,994 A * 1/1998 Pease et al. .................. 435/4

OTHER PUBLICATIONS

Sakaguchi M. Photoionization of Alkylphenothiazines in Vesicles. J Phys Chem 94:870–874, 1990.*

Ham G. Stability of Trace Iodine Solutions. Analytical Letters 12(A5):535–541, 1979.*

* cited by examiner

*Primary Examiner*—Ralph Gitomer
(74) *Attorney, Agent, or Firm*—Mark A. Litman & Assoc. P.A.

(57) ABSTRACT

Chemiluminescent detection of molecules of synthetic or natural origin such as proteins and nucleic acids (DNA and RNA), as well as other biologic molecules, is increasingly replacing radioactive detection as the method of choice where sensitivity is critical. In such assays, luminescence is customarily achieved by the oxidation of a luminol or isoluminol substrate in the presence of an oxidizing agent such as hydrogen peroxide or hydrogen peroxide source, such as perborate, and a peroxidase catalyst such as horseradish peroxidase. To obtain useful levels of luminescence (e.g., detectable levels) by customary techniques, a luminescent enhancer is also present during oxidation. It has been found in the practice of the present invention that azine enhancers have contained an impurity which reduces the properties of the chemiluminescent assay working solutions. The present invention describes a working solution, a process of using the working solution, and kits containing solutions which can be mixed to form the working solutions comprising a solution which is useful for the chemiluminescent assay of peroxidase activity comprising: a) at least one chemiluminescent cyclic diacylhydrazide, b) at least one azine enhancer, and c) at least one oxidizine agent wherein said azine enhancer comprises less than 0.005 parts mole/mole total basis of azine compounds having a hydrogen atom bonded to a nitrogen atom of the azine ring. It has generally been found that this hydrogen containing azine is a poisoning agent for the performance of the azine enhancer.

28 Claims, 13 Drawing Sheets

Relative intensity values for the Working Solution of the Present Invention when unexposed for 1 minute, 5 minutes or 30 minutes after 24 hours and 48 hours. No signal was beyond 6 hours with the Commercially Available Enhanced Luminol Based Working Solution at any of the film exposures.

Comparison of 1.5 mM Azine Enhancer 1c ± 0.0015 mM Azine Poison 1a
Signal Intensity at 3.9 pg of B-HRP over 2 Hours Comparison of 12 mM Azine Enhancer 2b ± 0.0015 mM Azine Poison 2a Signal Intensity at 3.9 pg of B-HRP over 2 Hours

ASSAY OF PEROXIDASE ACTIVITY

BACKGROUND OF THE INVENTION

1. Field of the Invention

The present invention relates to chemiluminescent systems, especially enhanced chemiluminescent systems for assay of peroxidase activity. For the purposes of this specification, "enhanced chemiluminescence" is defined by the fact that the total light output of the present invention and/or signal to noise ratio of the present invention is greater than the output given by a 2,3-dihydro-1,4-phthalazinedione/oxidizing agent/peroxidase solution in the absence of the luminescent enhancer. When a 2,3-dihydroxy-1,4-phthalazine dione is used in the "enhanced chemiluminescence" system, it may most accurately be compared to the same compound in the absence of a luminescent enhancer for comparison under this definition. More particularly, the present invention relates to such systems wherein increased light output is obtained, increased rates of attaining maximum light output may be obtained, and extended duration of light output can be achieved. In combination, these characteristics of the present invention achieve lower limits of detection and more useful assays. These improvements are due to the use of a single azine enhancer containing a water-soluble moiety. The invention also relates to the use of highly purified enhancers which significantly improve various properties associated with the chemiluminescence developed during the peroxidase catalyzed oxidation of a chemiluminescent compound such as luminol, isoluminol and their derivatives, such as chemiluminescent cyclic diacylhydrazides generally. The invention is particularly applicable to detection of proteins, nucleic acids and other analytes using all types of membrane-based assays such as dot blotting, western blotting, southern blotting, and northern blotting, etc. Furthermore, the invention is particularly applicable to the detection of proteins, nucleic acids, and other analytes using all types of solution-based, luminometric assays such as ELISAs (Enzyme Linked Immunoabsorbent Assays), coated tube assays, bead assays, etc.

2. Background of the Invention

Chemiluminescent detection of molecules of synthetic or natural origin such as proteins and nucleic acids (DNA and RNA), as well as other biologic molecules, is increasingly replacing radioactive detection as the method of choice where sensitivity is critical. In such assays, luminescence is customarily achieved by the oxidation of a luminol or isoluminol substrate in the presence of an oxidizing agent such as hydrogen peroxide or hydrogen peroxide source, such as perborate, and a peroxidase catalyst such as horseradish peroxidase.

To obtain useful levels of luminescence (e.g., detectable levels) by customary techniques, a luminescent enhancer is also present during oxidation. Among the enhancers which have been successfully used with peroxidases are aromatic amines (U.S. Pat. No. 4,729,950), phenols (U.S. Pat. No. 4,598,044), and azines (e.g., phenothiazines, phenoxazines) and phenolindophenols (U.S. Pat. No. 5,171,668).

Currently, in chemiluminescent assays for proteins, the assay system of choice is a horseradish peroxidase catalyst, a phenolic enhancer, and a hydrogen peroxide source. The peroxidase catalyst is generally coupled, directly or indirectly, to a ligand, (e.g., an antibody, having binding specificity for the protein of interest). In turn, the intensity of luminescent response from the oxidation of the substrate (e.g., the chemiluminescent cyclic diacylhydrazide, such as the luminol or isoluminol derivative) by the bound peroxidase catalyst in the presence of an enhancer is used as a measurement of the amount of protein.

Nucleic acids can be assayed in a similar manner to proteins. However, with nucleic acids the current chemiluminescent system of choice is an alkaline phosphatase catalyst and a phospho-substituted dioxetane substrate. In such systems, the light output is improved by the presence of certain flouorophore-containing micelles (Focus 12, Number 1, pp. 9–12).

While the above-described assays for proteins and nucleic acids are currently in use, their use is accompanied by certain drawbacks. For example, while chemiluminescent systems for assaying proteins using peroxidase can yield rapid luminescence, such luminescence is short lived and of modest intensity, and has significant limits in its ability to detect small amounts of the target analyte. Accordingly, a rapid measurement of luminescence intensity must be made and such a rapid measurement may not always be possible or desirable. Similarly, there are several limitations to the current chemiluminescent systems used for assaying nucleic acids. First, the alkaline phosphatase procedures are more expensive than the peroxidase catalyzed systems. In addition, the luminescence achieved is slow to develop, even though once developed, the luminescence continues for an extended period. Therefore, assays of long duration are required to achieve acceptable levels of sensitivity.

SUMMARY OF THE INVENTION

Now, however, in accordance with the present invention, there is provided an improved method for the chemiluminescent assay of peroxidase activity which is generally useful in connection with the detection of analytes of all types (e.g., biological macromolecules, organic molecules, natural or synthetic molecules, etc). The invention is particularly applicable to detection of proteins and nucleic acids using all types of membrane-based assays by techniques such as dot blotting, western, blotting, southern blotting, and northern blotting, colony filter hybridization, etc. Furthermore, the invention is particularly applicable to the detection of analytes using all types of solution-based, luminometric assays, such as ELISAs (Enzyme Linked Immunoabsorbent Assays), coated tube assays, bead assays, etc..

In the present specification, an unprecedented degree of luminescence is developed more rapidly than previously reported, and the intense luminescence persists for a period of time comparable to the dioxetanes (which is much longer than previously reported for peroxidase-based systems). Thus, by using the method of the present invention rapid development of a high intensity luminescence is achieved and said luminescence is of an extended duration. Thus, this method combines the advantageous features of both of the current chemiluminescent methodologies (those based on peroxidase or alkaline phosphatase catalysts). Moreover, by combining the features of high light output with extended duration, unprecedented levels of sensitivity are achieved in many assay systems.

In one of its aspects the present invention provides an improvement in the method for the chemiluminescent assay of peroxidase activity which involves oxidizing a substrate (e.g., 2,3-dihydro-1,4-phthalazinedione, chemiluminescent cyclic diacylhydrazide, luminol, isoluminol, or other derivatives) in a solution containing the substrate, the catalyst (e.g., peroxidase), an oxidizing agent (e.g., hydrogen peroxide or hydrogen peroxide source) and an enhancer (e.g., an azine such as a phenothiazine or phenoxazine). The improvement resides in the use, as the enhancer, of azines such as the phenothiazines or phenoxazines free of specific classes of compounds which adversely affect the performance of the entire system, and which have been found to be present in previous enhancer compositions. These compounds, which must be reduced in concentration from their levels in conventional enhancer preparations are azines in which the nitrogen atom of the azine ring has a hydrogen bonded directly thereto. It is also preferred to provide aqueous solutions of the substrate, oxidizing agent, and enhancer by using enhancers which contain a water-solubilizing substituent such as alkyl sulfonates salts, substituted ammonium salts, or phosphonium salts. A further limited aspect of the present invention resides in providing an aqueous solution useful for assaying peroxidase activity which consists essentially of a chemiluminescent cyclic diacylhydrazide, an oxidizing agent, and an enhancer containing a water solubilizing

BRIEF DESCRIPTION OF THE DRAWINGS

FIG. 6 shows a graphic comparison of 12 mM Azine Enhancer 2b (Poison-free) versus 12 mM of the Same Enhancer with 0.001 5mM Azine Poison 2a.

DETAILED DESCRIPTION

Figure 1:
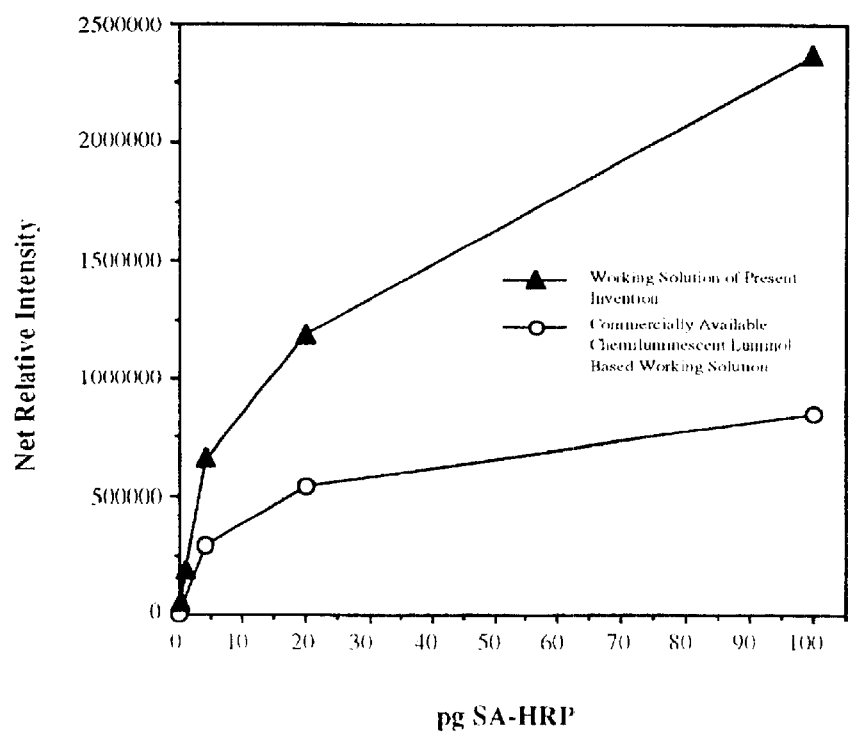
FIG. 1 shows luminescence achieved in the assay of various concentrations of SA-HRP using the substrate solution of the present invention in comparison to a commercially available solution.

The chemiluminescent assay solutions of the present invention may be generally described as a solution comprising:

1) at least one chemiluminescent compound which may be enhanced by the presence of an azine enhancer and an oxidizing agent,
2) an azine enhancer, and
3) an oxidizing agent.

The chemiluminescent assay solutions of the present invention may be more particularly described as a solution comprising:

1) at least one chemiluminescent linear hydrazide (e.g., a mononuclear monohydrazide) or cyclic diacylyhydrazide (alternatively referred to in the art as a 2,3-dihydro-1,4-phthalazinedione, comprising the class of luminol, isoluminol, salts and substituted derivatives of those compounds),
2) an azine enhancer (wherein said azine enhancer comprises, consists essentially of, or consists of luminescent rate inhibiting azine compounds having less than a 0.005 ratio on a molar/molar basis [which is less than 0.5%, which is less than 5 parts per 1000 parts] of azine enhancer having a hydrogen atom bonded to a nitrogen atom of the azine ring, as compared to the total molar content of azines), and
3) an oxidizing agent (preferably a peroxide compound such as hydrogen peroxide or hydrogen peroxide source).

An aspect of the present invention is the persistence which may be obtained in the chemiluminescent signal. In the previous art, at least one-half hour is required to reach maximum luminosity (although in some systems such as those employing phenolic enhancers, the maximum luminosity may be achieved more rapidly). Moreover, the peak signal diminishes fairly rapidly, typically within two to four hours with the more persistent peroxidase-based systems. The preferred embodiments of the present invention not only may provide higher absolute luminosities, but are able to display high intensity luminosity for extended periods of times, such as ten or more hours. For example, the most commonly used peroxidase assay commercial system based on U.S. Pat. No. 4,598,044 will reach peak luminosity within 5 minutes, and in less than four hours will display no useful luminosity. In some situations, the signal will be less than 50% of the peak intensity within one or two hours. The present system readily can be formulated to reach peak luminosity in less than ten minutes and maintain a level of at least 75% of that peak for 30 minutes, one hour, two hours, even four hours. In the most preferred systems of the present invention which are shown in detail in the examples, this luminosity can be maintained at greater than 80% of its maximum for more than one hour, or even more than two hours, and even greater than 85% or greater than 90% may be maintained for more than one hour and even more than two hours, with a level of greater than 75% continuing for up to four or six hours. This is a tremendous benefit to the operator since the latitude in taking the sample for measurements or evaluation is greatly increased. Rather than having to wait extended periods of time for peak intensity to be achieved and then having a narrow window, which may be as little as half an hour to take accurate and meaningful readings of the luminescence, the operator has many hours within which significant readings may be taken, with far less importance attached to the times of mixing and reading.

It is a finding of the present invention that azine enhancers, and particularly the preferred phenothiazine and phenoxizine class of azine enhancers used in the prior art may often contain impurities or trace impurities not removed by conventional purification methodologies employed in the art. In the present specification, said impurities have been shown to dramatically and adversely affect the performance characteristics of the entire chemiluminescent assay system. Specifically, it has been found that, compounds having a hydrogen atom bonded to the nitrogen atom of the azine ring are present in commercial preparations of phenothiazines (these azine impurities which adversely affect the performance of the chemiluminescent system are hereafter referred to as "poisoning azines"). Reconstruction experiments in which poisoning azines were added to highly purified preparations of phenothiazines (made using the preferred embodiment of this invention) indicate that the system is adversely affected when poisoning azines are present in amounts less than 0.5% of the total azine content. This amount, and even greater amounts present in commercially available azines, and have been found to: (1) Reduce the total luminescence of the system; (2) Increase the length of time necessary to achieve peak luminescence; and/or (3) Decrease the sensitivity of the assays which can be performed. Most significantly, prepartions of azines which were not highly purified contain varying amounts of poisoning azines leading to inconsistency in assay performance and reproducibility.

Therefore, an important aspect of the invention arises from the fact that there was no knowledge of the adverse effects produced by this specific contaminant(s) (the "poisoning azines") in chemiluminescent assay performance, there was no knowledge of the specific range of effects caused by these contaminants, and there was no knowledge of the concentration of contaminants which could be tolerated in the system. The degree of benefit provided by removal of the contaminant(s) species was unexpected, even after the nature of the contaminant(s) and its initial effects were discovered by applicants.

The contaminant has been identified as a reducing azine species wherein the azine is capable of donating an electron or otherwise reacting with oxidized peroxidase (or peroxidase equivalent). These poisoning azines are usually identifiable as having a nitrogen atom of the azine ring (e.g., the 10 position on the phenothiazine ring) substituted with a hydrogen atom. This characterization has been made both by theoretic analysis, chemical analysis to determine the presence of the 10=H species, and by reconstruction experiments wherein the "poisoning azine" was added to highly purified azine compositions in order to quantitate the poisoning effects, and to establish the preferred purity of the azine enhancers. From this work, it has been estimated in the practice of the present invention that reducing the ratio of the poisoning azine: azine enhancer to less than 0.5% (less than a molar ratio of 0.005% parts poisoning azine to total azine in the system) compared to the total amount of azine present in the solution provides significant (e.g., measurable) improvements over azine compositions in which the amount of the poisoning azine is greater than 0.5%. In the practice of the present invention; therefore, the ratio of poisoning azine to the total azine present in the solution (on a molar basis, unless otherwise stated) should be less than 0.005, preferably less than 0.003, more preferably less than 0.001, still more preferably less than 0.0005, and yet still more preferably less than 0.0003 and 0.0002. These proportions are also conveniently presented and more preferred maximum limits identified as less than 0.5%, less than 0.1%, less than 0.05%, less than 0.02%, less than 0.015%, less than 0.01%, and less than 0.005% parts (on a molar basis) of poisoning azine to total azine in solution. As noted above, there at least three benefits to the removal of the contaminants or the use of azine enhancers synthesized by processes which do not produce or leave as a residue or unreacted reagent the poisoning azine. First, commercial chemiluminescent products have required as much as a full thirty minute 'warm-up' period for peak luminosity to be achieved. The preferred composition of the present invention can attain peak luminosity and be used in less than 10 minutes, many compositions in less than 5 minutes, and some compositions in less than 3 minutes. Thus the rate of attaining luminosity is increased. Second, the level of luminosity (peak luminosity) can be dramatically increased, by factors of tens over previously described systems. Although part of the luminosity increase may be explained by the use of more soluble enhancers (and the resultant greater concentrations present), peak luminosity can not be explained as a mere concentration effect, particularly with the magnitude of the improvement in the present invention. Third, within the practice of the present invention, an increase in assay sensitivity can be obtained. Concentrations or absolute amounts of a target analyte, which are one-tenth the minimum detectable by other systems can be detected in preferred systems of the invention. In some cases the lower limit of detection may be 1% that of the lowest limit of detection obtained in other chemiluminescent assay systems. This is a two order of magnitude improvement in sensitivity, which can not be predicted from removal or the absence of impurities.

It is to be noted that only one species of azines has been found which has a hydrogen atom bonded to a nitrogen atom on the azine ring which does not poison the system. This species is a non-enhancing oxidized species of phenoxazines, phenoxazine-5-oxide. This is an oxidized species whose oxidation potential is too high to enable a reaction with oxidized peroxidase materials (or peroxidase equivalents). If the thiazine is oxidized, it apparently has an oxidation potential which is too high for reaction with oxidized peroxidase species. Since it does not react with the oxidized peroxidase species, the thiazine cannot poison the system, as that reaction appears to be part of the poisoning mechanism. Therefore, although only this oxidized species has been found to have an azine structure with a hydrogen atom bonded to the nitrogen atom of the azine ring and not be a poisoning agent, it is apparent that other azine species could exist which would not be poisoning species. As noted above, the synthesis of phenothiazine compounds appears to leave or create phenothiazines with a hydrogen atom bonded to the 10-yl position of the ring, and that this artifact of the procedure is clearly a poisoning species. Phenoxazine with a hydrogen in the 10-yl position has also been clearly proven to be a poisoning species. If a thiazine with a hydrogen in the 10-yl position is proven to be a non-poisoning species (by its inability to readily react with oxidized peroxidase at room temperature), its presence in or absence from the solution is inconsequential. In reciting the absence of azines with hydrogen bonded to nitrogen atoms in the azine ring, the addition of oxidized peroxidase inert compounds within this class are not to be considered in the consideration of proportions of the azines. By describing these compounds as inert or not readily reactive with oxidized peroxidase, the basis for the consideration of these terms is visible effects upon luminescence in a peroxidase system. That is, even if the compound will react with oxidized peroxidase over a period of time or in activating conditions (with additional heat [as compared to room temperature conditions], catalysis, special solvents rather than water, etc.), there must be a level of activity which creates a luminescent effect (diminishing the intensity of chemiluminescence or the rate of attainment of intensity) for the compound to be a poisoning azine species, and therefore necessarily excluded according to the practice of the present invention. Any such species in a concentration of 5% of total azine, for example, which reduces the rate of attainment of maximum intesnity by at least 5%, and especially by at least 10% (that is reduces the average slope of the plot of time (from time=0) versus light intensity) is defined as a poisoning species. Within the practice of the present invention, the term "poisoning azine" is defined as an azine which has a 10-yl hydrogen and reacts with the oxidized peroxidase species to cause these effects. As in the case of the single determined species which is does not poison the chemiluminescent reaction, any compound which does not poison the chemiluminescent reaction is excluded from the term "poisoning azine" in the definition of the present invention.

As noted above, the benefits of the removal of the contaminants or the use of azine enhancers which would be synthesized by processes which did not produce or leave as a residue or unreacted reagent the poisoning azine, may occur in one of at least three different technical areas. Commercial products have required as much as a full thirty minute 'warm-up' period for peak intensity of the chemiluminescent assays to be achieved. The preferred composition of the present invention can attain peak luminosity and be used in less than 10 minutes, many compositions in less than 5 minutes, and some compositions in less than 3 minutes. Thus the rate of attaining luminosity may be increased. The level of luminosity (peak luminosity) can be dramatically increased, by factors of tens or hundreds over commercial systems. Although part of the luminosity increase may be explained by the use of more soluble enhancers (and greater concentrations thereof), peak luminosity can not always be suggested or explained as a mere concentration effect, particularly with the magnitude of the improvement in many cases. Additionally, another area of benefit which is possible within the practice of the present invention is an increase in sensitivity, as measured by the capability of being able to detect lower amounts of targeted analyte, such as a protein by the assay process. Concentrations or absolute amounts of the targeted analytes which are one-tenth the lowest detectable limits of other systems can be detected in preferred systems of the invention. In some cases, the lower detectable limit may be 1% that of the lowest detectable limit of other chemiluminescent assay systems. That is two orders of magnitude improvement in sensitivity, which can not be predicted from removal or the absence of impurities. Concentrations of analytes such as proteins lower than 1.0 picograms can be readily identified with appropriate guiding antibodies or signal attaches to the peroxidase. Amounts of less than 0.1 picograms have been achieved, and even less than 0.05 picograms of materials have been detected by the practice of the most preferred aspects of the present invention.

A related aspect of the present invention concerns the high concentrations of azine enhancer and luminol-type material used. Where concentrations of the enhancer and/or luminol-type material are increased in the practice of the present invention, the peak luminosity can significantly exceed the proportional luminosity increase expected by mere increases in concentration. In fact, a critical aspect of this invention is that without achieving the enhancer purities reported herein, it would not be possible to utilize the high concentrations of azine enhancer. This is because typical prepartions of azines contain amounts of poisoning azines which would be completely deleterious to the level of luminosity achieved, resulting in poor assay sensitivity.

In part, the increased enhancer concentration is achieved through the use of water-solubilizing groups (for use in aqueous solutions) on the enhancers which allows for much greater concentrations of the enhancer in the solution. This has permitted the employment of extremely high enhancer concentrations thereby allowing the enhancer described in the current specification to be used as the sole enhancer, which led to the discovery of the superior performance, in chemiluminescent assays, of using a single azine enhancer at very high concentration. Critically, this discovery could not have been made using azines from coventional prepartions or of typical purity. Accordingly, the working solution (i.e., the final solution brought in contact with the peroxidase) consists essentially of substrate, oxidizing agent and the enhancer. As used herein, the phrase "consists essentially of" means that the named ingredients are necessary, but that other ingredients which do not detract from the attributes of the solution can also be present. The prior art (e.g., U.S. Pat. No. 5,171,668) has suggested maximum enhancer levels of 300 $\mu$M. However, the present invention allows for enhancer concentrations of at least 500 $\mu$M, preferably at least 800 $\mu$M, more preferably at least 1000 $\mu$M or 1200 $\mu$M, and even 1500 $\mu$M or more in aqueous solution in the practice of the present invention. The most preferred practice of the present invention has concentrations of at least 1500 $\mu$M of enhancer in aqueous solution.

As mentioned earlier, U.S. Pat. No. 5,171,668, assigned to Fujirebio (and hereafter also referred to as "Sugiyama" or the "Fujirebio patent"), discloses the use of phenothiazines and phenoxazines in peroxidase catalyzed assays based on the oxidation of a chemiluminescent 2,3-dihydro-1,4-phthalazinedione substrate such as luminol. Many phenothiazines and phenoxazines are shown without any reference as to whether they contain any charged moiety. In fact, the alkyl sulfonate derivatives are among the phenothiazines and phenoxazines disclosed in the patent, and are useful herein as azine enhancers.

The Fujirebio patent, however, does not illustrate the use of these compounds as a sole enhancer and the patent further fails to recognize the surprisingly superior performance, with respect to luminescent intensity and duration, when the azine enhancer is used alone and in extraordinarily high concentrations. In fact, all of the compounds disclosed by Sugiyama, including the phenothiazines and phenoxazines, were used in combination with phenolic enhancers, because synergistic effects between phenols and the test compounds were being evaluated. This line of inquiry was important because it explored the results achieved in chemiluminescent assays resulting from the use of combinations of enhancers. However, in looking for effects additive to those achieved with phenolic enhancers alone, Sugiyama was completely in keeping with the prior art, since a large body of previous literature clearly demonstrated the utility of phenolic enhancers in chemiluminescent assays of peroxidases. Therefore, an important aspect of the present invention is recognition that the "additive azine compounds" disclosed by Fujirebeo are superior in performance to the phenols when said azines are used alone, at high concentrations, and in extreme purity.

One additional aspect of the present invention which is unexpected given the performace of previously described chemiluminescent systems, is the shelf stability of Solutions A & B (later described) of the invention. Previously disclosed chemiluminescent assay compositions include systems comprising, for example, either:

1) chemiluminescent cyclic diacylhydrazides and phenolic enhancers;
2) chemiluminescent acridans; or
3) 1,2-dioxetanes.

The first system (number 1 above) must be stored at 4° C. (by manufacturer's instructions) to retain its functional capability for an extended time, for example 12 months. In fact, this composition loses a large percent of its activity if stored for even one day at room temperature. Users of the second and third systems are similarly advised to store these formulations at 4° C. to achieve 12 months of useful activity. All of these chemiluminescent systems (numbers 1–3 above) lose significant percentages (e.g., greater than 25%) of their acitivity when stored at 37° C. for a week. Significant losses are even notable in some of the compositions when stored at 37° C. for less than one week. In contrast, the composition of the present invention comprising the chemiluminescent acyl hydrazide (e.g., the linear or monocyclic monohydrazide, or the chemiluminescent cyclic diacylhydrazides) and the azine enhancer with reduced amounts of poisoning azine present have demonstrated stability (with a loss of less than 20%, even less than 15%, even less than 10%, or even less than 1% activity) with storage at 37° C. for twelve months. This provides a major improvement and convenience to the operator.

The enhancers, and especially the anionic enhancers of the present invention, may be prepared by conventional and customary derivatization techniques using commercially available phenothiazine or phenoxazine compounds. For example, see U.S. Pat. No. 5,445,755 and Bodea et al., vol. 9, Academic Press, N.Y., pp. 356–368, 389–393 (1968).

As noted above, the assay of the present invention may be performed in a number of different formats. Although some of the benefits of the present invention, especially more rapid light output, increased light output, more sustained light output, and improved shelf-life, are characteristics which may all be present in a composition of the present invention, there are other improvements possible with the present invention, which may be useful only in certain assay formats. For example, given the extreme sensitivity of the present invention, solution-based, luminometric assays, such as ELISAs, coated tube assays, bead assays, etc. are more susceptible to increased background (non-specific) luminosity than membrane-based assays. This may be due to the presence of divalent metal cations in Solutions A and B and/or the constituents thereof. The cost of complete removal of said cations from the solutions and/or the constituents would be prohibitive. However, it has been found in the practice of the present invention, particularly in combination with the highly purified azine enhancers, that the signal-to-noise (S/N) ratio is greatly increased by the inclusion of chelating agents for divalent metal cations. The addition of chelating agents to the Solutions A and B of the present invention may increase the signal-to-noise ratio by factors of more than 5, 10, 15 or even 20. This can be effected with concentrations of chelating agents on the order of at least 0.03 mM, better achieved with concentrations of at least 0.05 mM of chelating agent, still better effected with at least 0.075 mM of chelating agent, and best achieved with at least about 0.1 mM of chelating agent. There is some gradual reduction of net signal intensity at ever increasing amounts of some chelating agents, but even at concentrations of 0.80 mM, signal to noise ratios have still been imporved by a factor of more than 10 in some solutions. It is desirable to add the preferred amount of said chelator to Solution B of the present invention.

PREFERRED EMBODIMENT OF THE PRESENT INVENTION

In keeping with the present invention, the azines described herein are any enhancer compound which has at least one nucleus of an azine ring. Any substituent is considered an acceptable substitution which: (a) Does not compromise the enhancing function of the azine grouping; or (b) Cause the compound containing the grouping to be reactive with the oxidized peroxidase in such a way that the luminescence intensity or efficiency of the system is significantly inhibited/diminished of or completely eliminated for some period of time at room temperature (e.g., a poisoning species per the current disclosure).

Generally, such substitution includes alkyl groups (including skeletally substituted alkyl such as ether, polyethyleneoxide, thioether, amine, amide, etc.), which can be terminated with water solublizing groups (including sulfonate, substituted ammonium and phosphonium, electron donating groups, such as nitro, acyl, aroyl, halides, formyl, acylamide. These substituents can be attached directly to any part of the ring systems complementing the basic azine structure.

More specifically, such substitution is represented by the general structure shown in (1) below.

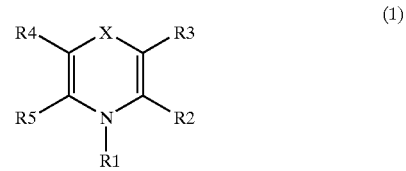

(1)

Where $R^1$–$R^5$ can be isolated substituents (as described above), or part of, or within a ring system which is preferably aromatic or heteroaromatic with substituents attached ($R^1$–$R^4$). These substituents are preferred based on their influence in controlling the ability of the enhancer to reduce/be oxidized by/transfer an electron to the oxidized peroxidase intermediates with respect to its redox properties, water solubility and its abilities to control its distance and orientation to the aforementioned oxidized peroxidase intermediate.

X is O, S, N—$R^1$, C—$NR^2$, C=$CR^2$, where R is H or $R^1$, CH=CH, $CR^1$=$CR^2$, with substituents from the electron donating class the preferences for $R^1$ and $R^2$.

A compound which has the central ring structure identified above is an azine compound according to the present invention. An azine compound which enhances chemiluminescence of a luminol based solution is an azine enhancer according to the present invention. An azine compound which has at least one fused ring attached to the azine nucleus is an at least monocyclic azine compound, and an azine which has at least two fused rings bonded to the azine nucleus is a dicyclic azine an at least polycyclic azine. The fused rings are preferably phenyl rings, but may be naphthyl, heteroaromatic rings, and the like, substituted or not.

The structures of the azine compounds identified generally in U.S. Pat. No. 5,171,668 are identified as useful enhancers in this application, preferably those containing the 10-propylsulfo-water solubilizing substituent. With the same proviso, useful phenothiazines and phenoxazines are illustrated in U.S. Pat. No. 5,445,755, assigned to Proctor and Gamble and entitled, "Detergent Compositions Containing A Peroxidase/Accelerator System Without Linear Alkylbenzenesulfonate". The disclosures of these patents relevant to the structures of useful enhancer compounds are herein incorporated.

Preferred water soluble enhancer compounds are the 3-(with non-10-H) and 10-alkysulfonates (present as its salt, e.g., sodium or potassium) phenothiazine and phenoxazine derivatives. The alkyl groups of which contain 1–12 carbon atoms which can be the same or different. Particularly preferred water soluble enhancers are where the alkylsufonate is n-propylsulfonate and especially the phenothiazine derivative. The water soluble phenothiazine and phenoxazine enhancers can be prepared by customary synthetic techniques using commercially available phenoothiazine or phenothiazine. See U.S. Pat. No. 5,445,755 and Bodea, et.al., *Advances in heterocyclic Chemistry*. Vol. 9, pp. 322–460; *J.Phys. Chem.*, 90, 2469–75(1986). In fashioning the working substrate solution of the present invention (enhancer, substrate, and oxidizing agent) the azine enhancer is present in a concentration of 1 $\mu$M–100 mM. Particularly outstanding results are obtained when the concentration is in excess of 300 $\mu$M and preferably at least 1 mM.

Oxidizing agents and peroxidase catalysts useful herein can be any of those which are indicated as useful in systems involving peroxidase catalysts. The patents heretofore referenced identify useful oxidizing agents and peroxidases. Preferred oxidizing agents are hydrogen peroxide and perborates such as sodium perborate. Horseradish peroxidase is the preferred catalyst.

The concentration of oxidizing agent in the working solution is generally 10 $\mu$M–300 mM, and usually 1 mM–10 mM. Using a preferred working solution of the present invention containing azine enhancer at a concentration in excess of 1 mM, detection of less than 1 picogram and generally less than 200 femtograms of peroxidase can be achieved reliably and with reproducibility.

Turning to the chemiluminescent substrate, any such compound is considered useful so long as it has chemiluminescent properties. The luminescent compounds within the preferred practice of the present invention are chemiluminescent cyclic diacylhydrazides (alternatively referred to in the art as a 2,3-dihydro-1,4-phthalazinedione, comprising the class of luminol, isoluminol, and substituted derivatives of those compounds). The luminol or isoluminol derivatives are those compounds which have the central nucleus of luminol or isoluminol, and have substituent groups on positions which do not destroy the luminescent properties of the underlying nucleus. Some substituents in certain positions may reduce the luminescence and not provide additional benefits, but are still acceptable in the practice of the present invention. Conventional substitution would include alkyl (especially lower alkyl of 1–4 carbon atoms), alkoxy (especially lower alkoxy of 1–4 carbon atoms), hydroxy, halogen (especially Cl, I, and Br), carboxyl and carboxylate, acyl, nitro, amino, and the like. These groups may or may not have significant effects upon the luminescence, but are still fundamentally luminol or isoluminol derivatives within the scope of the present invention.

This class of chemiluminescent substrates are also described in U.S. Pat. No. 4,598,044 and the salts thereof are particularly useful. Luminol, isoluminol and the sodium salts thereof are particularly preferred in the present invention. The substrate can be included in the working solution at a concentration of 0.5 $\mu$M–200 mM. When using the higher and preferred concentrations of enhancer, chemiluminescent substrate concentrations of 0.1 mM–10 mM are most useful.

In preparing the working solution of this invention, it is customary for the operator to mix two separate, previously prepared solutions; one solution containing the chemiluminescent substrate and azine enhancer (Solution A) and the other containing the oxidizing agent (Solutiuon B). The solutions should be appropriately buffered to maintain a working solution pH of 6–12, preferably 7–9.5. Suitable buffers are well known and include citrate, acetate, Tris [Tris(hydroxymethyl) amino methane], borate, carbonate and phosphate, with the preferred buffer being Tris. In general the working solution is completely aqueous, though in order to achieve solubility of an enhancer, it may be necessary to include organic solvents such as dimethyl sulfoxide (DMSO). The working solution may be generally used at a temperature of 10–50° C., although 20–37° C. is preferred.

Any of the known classes of chelating agents known to be effective in the sequestering of divalent metal cations are useful in the practice of the present invention. A chelator which might react (with adverse effects on the entire chemiluminescent system) with the oxidized peroxidase material or another component of the system should, of course, be avoided. However, an appropriate selection can be readily made by those of ordinary skill in the art. Such chelating agents as nitriloacetic acid, and aninocarboxylic acids are representative of chelating agents which may provide these benefits. The poly (more than two) aminocarboxylic acids (and their salts, especially alkali metal salts, which are included within the term unless specifically excluded) are especially preferred, with representative compounds being selected from EDTA (ethylenediamine tetraacetic acid), DTPA (diethylenetriaminepentaacetic acid), TTHA (triethylenetetraamine hexaacetic acid), EGTA and PTPA (propylenetriaminepentaacetic acid). A thorough list of these chelating agents is provided in U.S. Pat. No. 5,013,622.

The Examples hereinafter presented illustrate the present invention in connection with membrane-based assays of peroxidase activity wherein the catalyst is bound (i.e., by chemical bonds or through physical interactions) to a membrane.

As shown, the combined desirable features of rapid development of intense luminescence and the extended duration thereof is achieved in such assay. However, the invention is also useful in other applications involving the assay of peroxidase activity such as all types of solution-based, luminometric assays.

The following examples illustrate the present invention. Parts and percentages are by weight unless otherwise indicated. Molar concentrations ($\mu$M or mM) are given.

The general range of operating conditions for the solutions of the present invention is described below.

Temperature
Optimal: 10–50° C.
Preferred: 20° C.–37° C.

pH
Optimal: 6–12
Preferred: 7.0–9.5
Suitable Buffers include but not limited to
citrate, acetate, Tris, borate, carbonate and phosphate
Peroxidase: 25 femtogram to 5 $\mu$g peroxidase labeled protein
 (higher if detected by naked eye).

Oxidant:
Optimal: 10 $\mu$M–300 mM
Preferred: 1 mM–10 mM
Luminol
Optimal: 0.5 $\mu$M–200 mM
Preferred: 0.1–10 mM Enhancer
Optimal: 1 μM–100 mM
Preferred: 10 μM–10 mM The concentration of the enhancer may vary with individually selected species of the azine enhancers. In aqueous solutions, higher concentrations may be provided by the use of ionic group substituted azines or water-solubilizing group-substituted azines. As shown in the description of the azines, ionic groups (such as acids, salts, amines, etc.) or water solubilizing non-ionic groups (e.g., the polyalkyleneoxides, preferably with a significant content of polyethyleneoxide, such as polyethylene glycol chains) may be used to increase the solubility of the enhancer. Although unsolubilized enhancers may achieve maximum concentrations of 20 or 30 microMolar (in spite of suggestion in some literature that concentrations of 300 microMolar is possible, the enhancers of the present invention may be used in concentrations of greater than 500, preferably greater than 1000, and in some instances preferably greater than 1200 microMolar. An optimized solution with water-soluble phenothiazines is provided with a concentration of 1500 microMolar azine. The actual solubility and use of the phenothiazine and phenoxazine has been observed at level of 30,000 microMolar solutions. There is no continuing increase in intensity at these very high levels, and even some noticeable drop-off, but the systems still perform, and in many cases at levels superior to the performance of competing commercial systems. The optimum level for concentration will often vary from enhancer compound to enhancer compound, especially as between different classes of enhancers. For example, peak intensity and the maximum rate of approaching peak luminosity are achieved at lower concentrations of phenothiazine than for phenoxazines. The chemiluminescent reactions described within utilizes a binding of protein or nucleic acid to a membrane and detection through a peroxidase label. The chemiluminescent reaction is initiated by the addition of the oxidant, chemiluminescent DPD and sensitivity enhancer on the membrane. The reaction is instantaneous and continues to produce light over time. The means for detection includes but is not limited to film, a phospho-imager or a CCD camera.

The chemiluminescent assay of the present invention can be used in the following types of blotting applications: Western Blot, Dot Blot; Southern Blot, Northern Blot or other membrane-based system utilizing a labeled peroxidase enzyme. Typical blotting applications are outlined below:

Western Blot (Towbin reference)

Protein is detected in a western blot by first separating protein samples electrophoretically on a SDS polyacrylamide gel. The proteins are then transferred electrophoretically to a membrane such as nitrocellulose. The nonspecific sites are blocked with a protein solution which has no active part in the specific immunochemical reaction of a particular assay. A specific protein of interest is detected then by the addition of an antibody made against the protein. After a wash step to remove any unbound antibody, a peroxidase labeled antibody is added that will react with the primary antibody. the unbound enzyme labeled antibody is removed by a series of wash steps. The membrane is then exposed to the chemiluminescent substrate to produce light. The membrane is then exposed to film or other detection medium for detection.

Dot Blot

Proteins are directly applied to a membrane and detected with an antibody system described above.

Southern Blot (Southern Reference)

DNA is detected in a Southern blot by first separating the DNA sample electrophoretically on an agarose gel. The DNA is then transferred to a membrane such as charge-modified nylon. The DNA is then fixed by irradiation or baking. The membrane is then blocked with a prehybridization buffer to prevent any nonspecific binding of a DNA probe. The DNA probe coupled ot a detectable label such as biotin is then added to the membrane and is allowed to incubate for several hours at 50° C. or higher. The blots then undergo a series of stringency washes to remove any nonspecific hybridized probe from the DNA target while maximizing target/probe interactions. The blots are blocked again to prevent any nonspecific binding of the enzyme labeled probe. A peroxidase labeled conjugate such as streptavidin peroxidase is added to the membrane. The membrane is washed to remove any unbound label. The membrane is then exposed to the chemiluminescent substrate to produce light. The membrane is then exposed to film or other detection medium for detection.

Northern Blot (Alwine Reference)

RNA is detected in a Northern blot by separating RNA samples and detecting with a DNA or RNA probe using a method similar to the Southern Blot application. Care must be taken to remove all ribonucleases which can interfere and destroy the target.

ELISAs

Enzyme Linked Immunosorbent Assays (ELISAs) utilize an enzyme label for the detection of proteins in a solid phase microtier plate system. Typically, a specific antibody is passively absorbed to the microtier plate. The nonspecific sites are blocked with a protein solution which has no active part in the specific immunochemical reaction of a particular assay. A specific protein of interest is captured by the antibody on the surface of the membrane and then detected by another antibody with an enzyme label. The enzyme label is reacted with a chemiluminescent substrate and detected in a luminometer.

Materials
Aldrich
N-Methylphenothiazine, phenolindophenol, luminol, sodium perborate.

Sigma
hydrogen peroxide, Kodak GBX Developer/Replenisher, Kodak GBX
Fixer/Replenisher, Actin from Rabbit Heart.

Pierce
Nitrocellulose membrane, horseradish peroxidase labeled streptavidin, tris buffered saline, human wild-type p53 baculovirus lysate, Lane marker Reducing Sample Buffer, Blocker™ Casein in PBS, Tween® -20, Mouse anti-p53, Horseradish Peroxidase labeled Goat anti-Mouse, Diodyne B® membrane.

Amersham
ECL Substrate

DuPont/NEN
Reflection™ X-ray film

Novex
4–20% heterogeneous SDS polyacrylamide gel and 12% homogenous SDS polyacrylamide gel.

ICN
Mouse anti-Actin (Clone C4)

Gibco
1 kilobase DNA ladder

Sodium phenothiazine 10-yl propane sulfonate was obtained by procedures reported by Sakaguchi, et al., *J. Phy. Chem.*, 94, 870–874 (1990) or common routes based on reaction of phenothiazine in the presence of base.

Sodium luminol was obtained from Sigma by recrystallization from 10% sodium hydroxide and water following treatment with Darco or the protocol according to Ham et al., *Anal. Lett.*, 12, 535 (1979).

2-chloro-10 (3 trimethyl amino propyl)-phenothiazonan bromide was prepared by heating phenothiazine and 4-bromobutyronitrile (Aldrich) together in DMF with potassium carbonate as base. The corresponding 19-(4-cyanopropyl) phenothiazine was hydrolyzed in hot 6 N HCl and purified by standard silica gel chromatography.

Instrumentation

Dot blot applications were performed using a Pierce Easy-Titer™ ELIFA Unit. Gel electrophoresis and transfer for western blot was done using Novex minigel apparatus. Hybridization for a Southern Blot was done in a Hybaid Hybridization Oven Model H9320. Densitometry was performed using a Hewlett packard Densitometer or a Microtek Scanner from Microteck. Collage™ densitometry software from Fotodyne was used for the relative intensity determination.

In the practice of the present invention, comparisons are made in terms of Relative Light Units (RLU) and between enhancer systems other than those of the present invention, and specifically in some instances to assay systems described in U.S. Pat. No. 4,598,044. Relative Light Units as defined by MLX Microtiter® Plate Luminometer (Dynex Technologies) is the intensity of emitted light, measured in units of Relative Light. To determine a comparative standard formulation for such Relative Light Units in the practice of the present invention for the RLU developed for the Examples of the present invention, the Working Solution of the present invention (See Example 1) was compared to a working solution of Hydroxycinnamic Acid in a working solution defined by an example of an enahncer system in U.S. Pat. No. 4,598,044. 15.6 picograms (pg) of Biotinylated HRP was added to either 100 µl of Working Solution of the Present Invention or to 100 µl of the Hydroxycinnamic Acid Working Solution and read at room temperatureon a MLX Microtiter® Plate Luminometer at 0.20 seconds/well on Autogain setting.

Hydroxycinnamic Acid Working Solution
0.5 mM Hydroxycinnamic Acid (Aldrich)
0.01% Hydrogen Peroxide
0.24 mg/ml sodium luminol The Working Solution of the present invention resulted in 71.6 Net RLU at 15.6 pg compared to 4.0 Net RLU for the Hydroxycinnamic Acid. This shows a 17.9 fold increase in net luminosity between the two chemiluminescent working solutions.

EXAMPLE 1

Signal Intensity and Sensitivity of System

This example illustrates the increased luminosity and sensitivity of the present invention. Various concentrations of horseradish peroxidase labeled streptavidin (SA-HRP) were filtered through a nitrocellulose membrane using an Easy-Titer™ ELIFA unit (see U.S. Pat. No. 5,219,528). The membrane was washed with tris buffered saline and removed from the unit. The membrane was cut into identical strips and incubated with a commercially available luminol based chemiluminescent system which is protected by U.S. Pat. No. 4,598,044 and with the working solution (Solutions A and B, mixed 1:1) in accordance with the present invention having the composition indicated below.

Working Solution of Present Invention

Solution A
5 mM Sodium Luminol
1.5 mM Azine Enhancer 1c
0.2 M Tris
pH 9.5

Solution B
4 mM Sodium Perborate
50 mM Sodium Acetate
pH 5.0

The membranes strips were removed from the working solutions, placed in plastic sheet protectors and exposed to x-ray film for 1 minute. The film was developed using traditional methods and scanned by a reflectance densitometer (Hewlett Packard). The relative intensities were determined using Collage™ Software from Fotodyne. FIG. 1 illustrates the dose response curves for both working solutions. The lower limit of detectability was calculated using the method of Rodbard "Statistical Estimation of the Minimal Detectable Concentration ('sensitivity") for Radioligand Assays" . Anal. Biochem, 90,1–12 (1978). Using the working solution of the present invention, SA-HRP could be detected down to 117 femtograms in comparison to the use of the commercially available reagent which could detect down to 3,400 femtograms.

The working solution of the present invention and the commercially available chemiluminescent working solution as described above were prepared and added to a white microtiter plate (100 µl/well). The background Relative Light Units (RLU) were determined on a Dynex MLX Microtiter® Luminometer. Biotinylated horseradish peroxidase (B-HRP) was added to the wells (10 µl/well) and mixed with the working solutions. The net RLU were calculated for both working solutions at 250 pg (Table 1) to illustrate the enhanced signal with the working solution of the present invention

TABLE 1

| Working solution | Net RLU at 250 pg of B-HRP | |
|---|---|---|
| Working Solution of the Present Invention | 1078.93 | |
| Commercially Available Luminol Based Working Solution | 36.90 | |
| | 29.23 | fold increase in net RLU |

EXAMPLE 2

Demonstration of Increased Signal to Noise with EDTA Addition The working solution of the present invention as described in Example 1 was prepared with various concentrations of EDTA and added to a white microtiter plate as described above. The signal RLU and background noise was determined for the working solution of the present invention with the various concentrations of EDTA (Table 2). The Signal to Noise ratios with the addition of EDTA to the working solution of the present invention clearly shows the improvement made by the addition of at least 0.1 mM EDTA when using a luminometer based application. This improvement is not demonstrated in the blotting application because of the inherent low background of the working solution of the present invention on the membranes.

TABLE 2

| EDTA (mM) | Signal | Noise | Signal/Noise Ratio |
|---|---|---|---|
| 0.00 | 17.67 | 4.68 | 3.77 |
| 0.10 | 9.16 | 0.47 | 19.68 |
| 0.20 | 8.94 | 0.47 | 19.06 |
| 0.40 | 8.00 | 0.36 | 22.14 |
| 0.06 | 7.03 | 0.40 | 17.60 |
| 0.80 | 6.18 | 0.36 | 17.10 |

EXAMPLE 3
Kinetics of Working Solution System

This Example illustrates the extended duration of luminosity achievable with the use of a working solution solution of the present invention. A Western Blot format was utilized.

Figure 2:
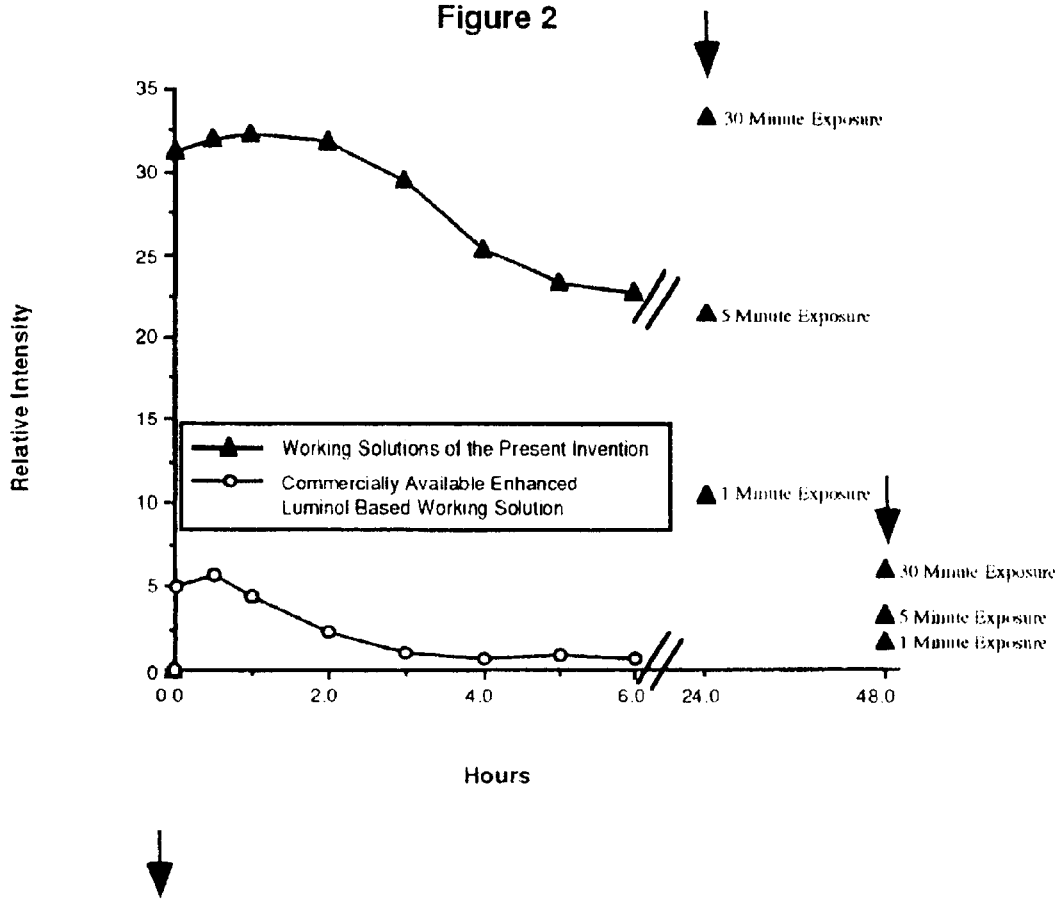
FIG. 2 shows the Relative Intensity of luminescence over time of a substrate solution of this invention compared with a commercially available substrate solution exposed for five minutes.

2.5 ng of actin from rabbit heart was separated electrophoretically on 4–20% SDS polyacrylamide gels and then as described in Example 1 was prepared and added to one of the membranes for 5 minutes. The commercially available working solution described in Example 1 was also prepared and added to the other membrane. The membranes were then placed between clear plastic sheets and exposed to film for 1 minute. The membranes were exposed again to film at various times over a 6 hour period (1 minute exposure) and also after 24 hours and 48 hours (1 minute, 5 minute and 30 minute exposures). These films were developed and scanned (BioRad Moldel GS700 Imaging Densitometer) to determine relative intensity. The results are shown in FIG. 2 which illustrates the extended duration of luminescence achievable with the use of the working solution of the present invention. The signal intensity generated by the working solution of the present invention was significantly higher than that of the commercially available product and the duration of luminescence was markedly increased.

EXAMPLE 4
Increased Stability of the Chemiluminescent System

This example illustrates the increased stability of the present invention compared to the commercially available chemiluminescent systems for both horseradish peroxidase and alkaline phosphatase.

The Working solution of the present invention was prepared as two reagents (Solution A and Solution B) and incubated at 4° C., Room Temperature and 37° C. over an extended period of time.
Solution A
10 mM Sodium Luminol
3 mM Azine Enhancer 1c
0.4M Tris
pH 9.5
Solution B
8 mM Sodium Perborate
100 mM Sodium Acetate
pH 5.0

Commercially available chemiluminescent working solutions components including a luminol based system as described in Example 1, a 1,2-dioxetane based system (Campbell, A. K., L. J. Kricka, and P. E. Stanley ed. Bioluminescence and Chemiluminescence, Fundamentals and Applied Aspects, Proceedings of the 8th Intern Symposium on Bioluminescence and Chemiluminescence. Sep. 1994 p 56–59) and were stored at 4° C. and at 37° C. up to 3 days. Each of the working solutions were tested in a microtiter plate format as described in Example 1. Table 3 shows the decrease in RLU at 250 pg of B-HRP for the Luminol Based and the 1,2-Dioxetane Based systems an indication of decreased stability. The working solution of the present invention was stable over the 3 day period tested. The Working solution of the present invention was also tested for luminosity and sensitivity over a 12 month period of time at both room temperature and 37° C. The results showed that the working solution of the present invention is stable for at least 12 months as indicated by unchanged luminosity and sensitivity and can be stored at room temperature. The other commercially available working solutions require 4° C. storage and some are limited to 6 months of stability.

TABLE 3

| Working solution | Length of Time | RLU of 250 pg B-HRP after storage at 4° C. | RLU of 250 pg of B-HRP after storage at 37° C. | % Change |
|---|---|---|---|---|
| Working solution of Present Invention | 3 days | 1488.03 | 1476.50 | 0.01% |
| Working solution of Present Invention | 12 months | * | * | * |
| Commercially Available Luminol Based System | 3 days | 53.13 | 45.06 | 15% |
| Commercially Available Dioxetane Based System | 1 day | 102.88 | 87.60 | 15% |

*Analysis performed in a blotting application over a 12 month period of time indicates that the sensitivity and luminosity of the working solution of the present invention is essentially unchaged after greater than 12 months at room temperature and at 37° C.

EXAMPLE 5
Concentration Effects of Azine Enhancers

This example describes the signal luminosity and sensitivity with increased concentrations of preferred azine enhancers.

Figure 3:
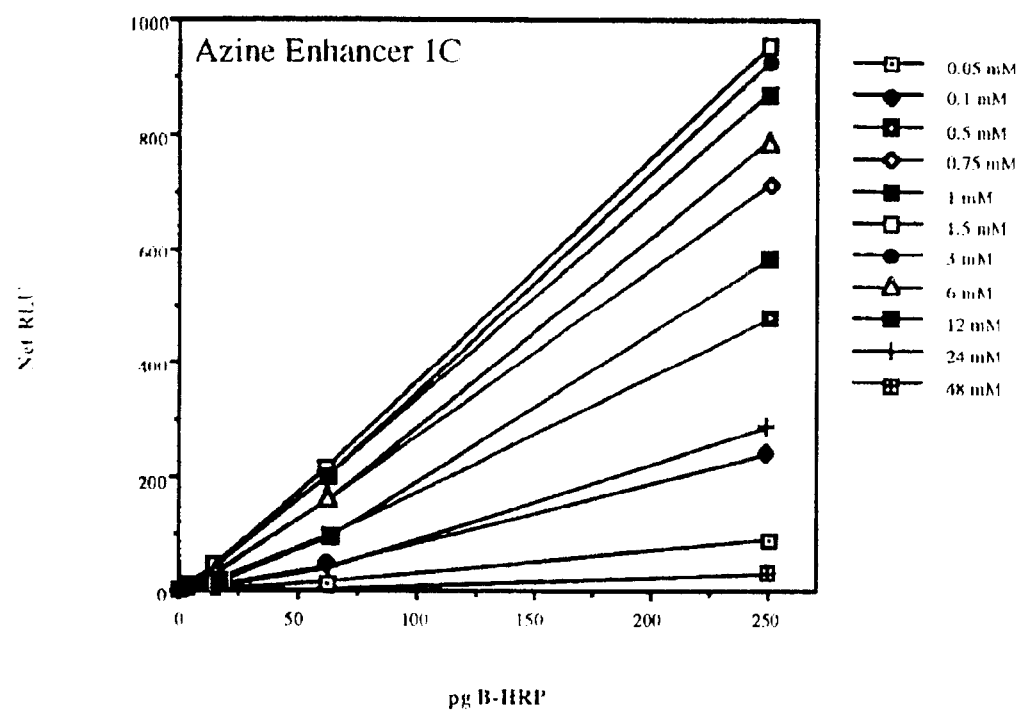
FIG. 3 shows Net RLU (intensity of luminescence) achieved with substrate solutions containing azine Enhancer 1c of the present invention at various concentrations.
Figure 4:
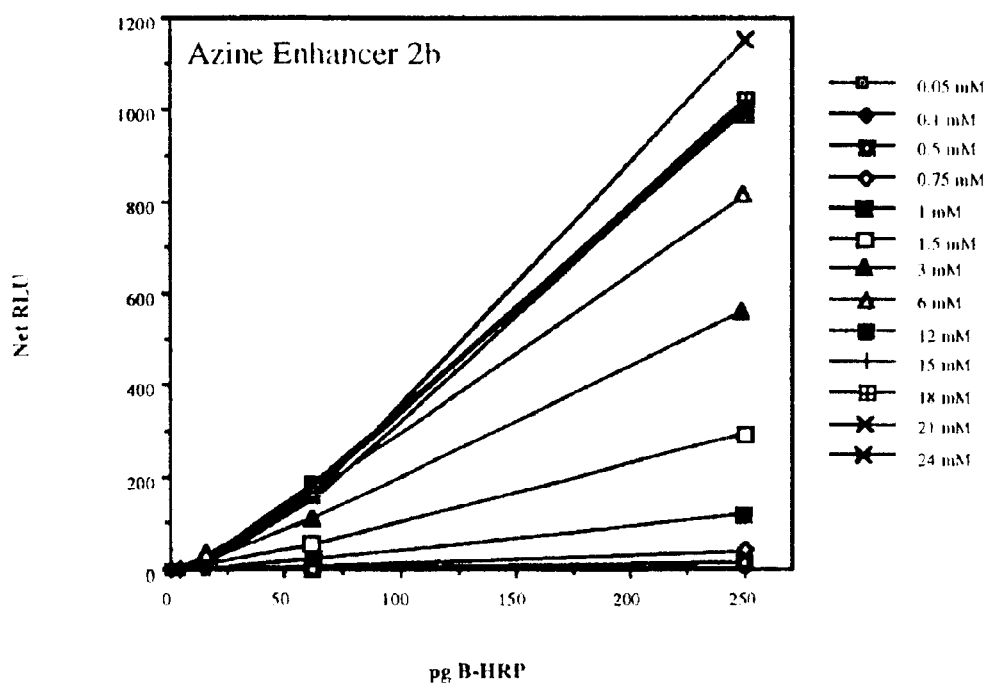
FIG. 4 shows Net RLU (intensity of luminescence) achieved with substrate solutions containing azine Enhancer 2b of the present invention at various concentrations.

The working solution of the present invention as described in Example 1 was prepared with various concentrations of Azine Enhancer 1c or Azine Enhancer 2b and tested in a microtiter plate application as described in Example 1. FIGS. 3 and 4 illustrates the dose response curves with Azine Enhancer 1c and Azine Enhancer 2b respectively. Tables 4 and 5 compare background signal, the signal of B-HRP at 250 pg and the estimated lowest detectable limit of B-HRP above background for Azine Enhancer 1c and Azine Enhancer 2b respectively. Azine Enhancer 1c reached a peak net luminosity at 1–3 mM. With increasing concentrations Azine Enhancer 1c, the luminosity was decreased. The lowest detectable limit of B-HRP was demonstrated with 0.75–1.5 mM Azine Enhancer 1c. Azine Enhancer 2b reached a peak net luminosity at 10–12 mM. With increase Azine Enhancer 2b (12 mM->24 mM), the luminosity remained at the same constant. Azine Enhancer 2b demonstrated the lowest detectable limit of B-HRP above background with >1.5 mM.

TABLE 4

| Azine Enhancer 1c Concentration | RLU at 250 pg of B-HRP | Background RLU at 0 pg of B-HRP | Lowest Detectable Limit of B-HRP above Background (pg) |
|---|---|---|---|
| 0.05 mM | 98.57 | 7.00 | 15.60 |
| 0.10 mM | 248.05 | 8.23 | 3.90 |
| 0.50 mM | 486.10 | 9.42 | 0.98 |
| 0.75 mM | 722.21 | 9.27 | 0.24 |
| 1.00 mM | 884.82 | 10.55 | 0.24 |
| 1.50 mM | 965.59 | 8.66 | 0.24 |
| 3.00 mM | 933.52 | 6.94 | 0.98 |
| 6.00 mM | 793.92 | 4.47 | 0.98 |
| 12.00 mM | 585.51 | 2.11 | 3.90 |
| 24.00 mM | 290.50 | 2.39 | 0.98 |
| 48.00 mM | 31.38 | 0.17 | 3.90 |

TABLE 5

| Azine Enhancer 2b Concentration | RLU at 250 pg of B-HRP | Background RLU at 0 pg of B-HRP | Lowest Detectable Limit of B-HRP above Background (pg) |
|---|---|---|---|
| 0.05 mM | 6.44 | 3.64 | 62.5 |
| 0.10 mM | 9.25 | 3.84 | 62.5 |
| 0.50 mM | 18.50 | 3.96 | 15.6 |
| 0.75 mM | 46.13 | 4.34 | 15.6 |
| 1.0 mM | 122.35 | 4.18 | 3.9 |
| 1.5 mM | 300.61 | 4.70 | 3.9 |
| 3 mM | 567.09 | 3.91 | 0.98 |
| 6 mM | 820.12 | 2.79 | 0.98 |
| 12 mM | 996.96 | 1.56 | 0.98 |
| 15 mM | 1015.36 | 1.12 | 0.98 |
| 18 mM | 1025.22 | 0.72 | 3.90 |
| 21 mM | 1018.36 | 0.49 | 0.98 |
| 24 mM | 1007.7 | 0.29 | 0.98 |

EXAMPLE 6
Controlled Poisoning of Working Solutions Containing High Purity Azine Enhancer with Poisoning Azines This example illustrates the affect of phenothiazine 1a or phenoxazine 2a as poisoning azine impurities on the working solutions in the present invention.

Figure 5:
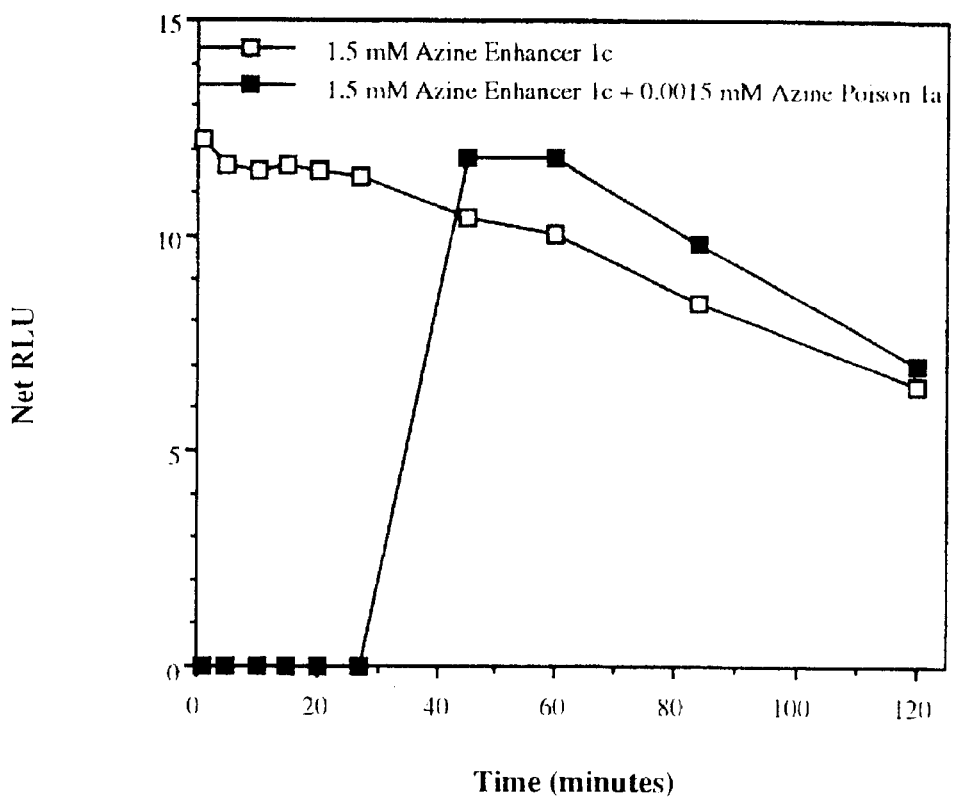
FIG. 5 shows the Net RLU for a specific azine Enhancer 1c with comparison between a purified and poisoned composition over time.
Figure 6:
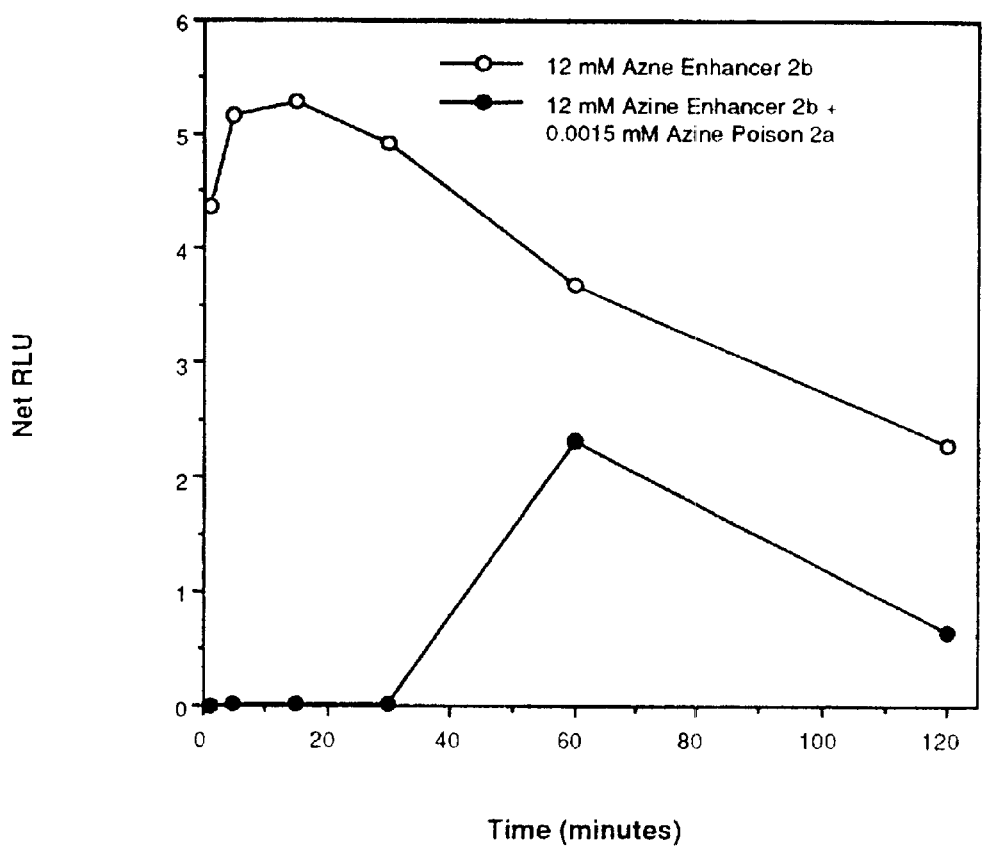

Azine Enhancer 1c and 2b were added as azine poisons at various concentrations to the working solution solution of the present invention as described in Example 1. Azine Poison 2a was also added at various concentrations to the following working solution:
Azine Enhancer 2b Working solution
5 mM Sodium Luminol
12 mM Azine Azine Enhancer 2b
0.2 M Tris
4 mM Sodium Perborate
50 mM Sodium Acetate The working solutions were prepared with and without the "azine poisons" and added to a microtiter plate. B-HRP at various concentrations was added to the working solution and mixed as in Example 1. The RLU were determined on a luminometer. Table 6 describes the affect that Azine Poison 1a and Azine Poison 2a have on the working solution of the present invention (Azine Enhancer 1c). Table 7 describes the affect that Azine Poison 2a has on the Azine Enhancer 2b working solution. FIG. 5 illustrates the affect that Azine Poison 1a has on the Azine Enhancer 1c working solution over a 2 hour time period at 3.9 pg B-HRP. FIG. 6 illustrates the affect that Azine Poison 1a has on the Azine Enhancer 2b working solution. Table 8 compares the working solution of the present invention with various concentrations of Azine Enhancer 1c with and without the addition of Azine Poison 1a.

TABLE 6

Microtiter Plate Assay

| Azine Poison (mM) + 1.5 mM Azine Enhancer 1c | RLU of 250 pg of B-HRP | Background RLU at 0 pg of B-HRP | Lowest Detectable Limit of B-HRP above Background (pg) |
|---|---|---|---|
| 0 mM Azine Poison (Control) | 1204.00 | 7.49 | 0.06 |
| 0.0015 mM Azine Poison 1a | 1141.75 | 0.09 | 15.6 |
| 0.0005 mM Azine Poison 1a | 1226.88 | 0.10 | 0.98 |
| 0.00017 mM Azine Poison 1a | 1257.34 | 0.31 | 0.98 |
| 0.000019 mM Azine Poison 1a | 1264.05 | 7.48 | 0.98 |
| 0.0015 mM Azine Poison 2a | 1055.97 | 0.53 | 250 |
| 0.0005 mM Azine Poison 2a | 1167.93 | 0.13 | 62.5 |
| 0.000167 mM Azine Poison 2a | 1228.52 | 0.15 | 3.9 |
| 0.000055 mM Azine Poison 2a | 1232.71 | 3.66 | 0.98 |
| 0.000019 mM Azine Poison 2a | 1228.28 | 7.28 | 0.98 |

TABLE 7

Microtiter Plate Assay

| Azine Poison (mM) + 1.5 mM Azine Enhancer 2b | RLU of 250 pg of B-HRP | Background RLU at 0 pg of B-HRP | Lowest Detectable Limit of B-HRP above Background (pg) |
|---|---|---|---|
| 0 mM Azine Poison (Control) | 821.99 | 1.47 | 0.061 |
| 0.0015 mM Azine Poison 2a | 578.76 | 0.046 | 62.5 |
| 0.0005 mM Azine Poison 2a | 785.93 | 0.085 | 15.6 |
| 0.00017 mM Azine Poison 2a | 793.57 | 0.313 | 0.24 |
| 0.000055 mM Azine Poison 2a | 830.29 | 1.21 | 0.24 |
| 0.000019 mM Azine Poison 2a | 866.85 | 1.08 | 0.24 |

TABLE 8

Microtiter Plate Assay

| Working solution | 0.00 mM Azine Poison 1a "no poison" | | | +0.0015 mM Azine Poison 1a "poison" | | |
|---|---|---|---|---|---|---|
| | RLU at 250 pg of B-HRP | Background RLU at 0 pg of B-HRP | Lowest Dectectable Limit of B-HRP above Background | RLU at 250 pg of B-HRP | Background RLU at 0 pg of B-HRP | Lowest Dectectable Limit of B-HRP above Background |
| 6 mM Azine Enhancer 1c | 556.7 | 6.25 | 3.9 pg | 522.89 | 0.24 | 250 pg |
| 1.5 mM Azine Enhancer 1c | 687.5 | 12.39 | 3.9 pg | 497.46 | 0.17 | 62.5 pg |
| 0.38 mM Azine Enhancer 1c | 567.16 | 10.93 | 3.9 pg | 0.93 | 0.25 | 62.5 pg |
| 0.19 mM Azine Enhancer 1c | 447.70 | 11.97 | 0.98 pg | 0.77 | 0.33 | 250 pg |
| 0.10 mM Azine Enhancer 1c | 210.36 | 14.95 | 3.9 pg | 0.55 | 0.35 | 250 pg |
| 0.05 mM Azine Enhancer 1c | 91.899 | 9.01 | 3.9 pg | 0.44 | 0.40 | 250 pg |

A dot blot assay as described in Example 1 was performed. The working solution of the present invention was prepared with various concentrations of Azine Poison 1a. The blot was incubated with the different working solutions of the present invention for 5 minutes and then exposed to film. The film was scanned on a BioRad Model GS700 Imaging Densitometer. Table 9 summarizes the affect that the Azine Poison 1a has on the working solution of the present invention.

TABLE 9

Dot Blot Assay

| Azine Poison 1a (mM + 1.5 mM Azine Enhance 1c | Relative Intensity at 250 pg of B-HRP | Background RI at 0 pg of B-HRP | Lowest Detectable Limit of B-HRP above Background (pg) |
|---|---|---|---|
| 0 mM Poison (Control) | 186.26 | 7.63 | 0.06 |
| 0.0015 mM Azine Poison 1a | 165.28 | 7.24 | 0.98 |
| 0.0005 mM Azine Poison 1a | 180.38 | 7.74 | 0.24 |
| 0.00017 mM Azine Poison 1a | 209.39 | 6.15 | 0.24 |
| 0.000055 mM Azine Poison 1a | 186.08 | 6.01 | 0.06 |

EXAMPLE 7

Working solution of Present Invention Compared to Preferred Working Solutions Described in U.S. Pat. No. 5,171,668

Horseradish peroxidase labeled streptavidin (SA-HRP) was filtered through a nitrocellulose membrane as described in Example 1 and the membrane cut into 5 identical strips. The working solution of the present invention as described in Example 1 was prepared along with working solutions containing other enhancers.

The Working Solution of the Present Invention was prepared as in Example 1 along with Azine Enhancer 1c (Low Concentration) Working Solution which was prepared from a 5 mM solution of Luminol in DMSO, a 5 mM solution of Azine Enhancer 1c in DMSO, a 0.1% hydrogen peroxide solution in 50 mM Tris, pH 8.5 and a 50 mM Tris pH 8.5 dilution buffer to have the following composition.

Azine Enhancer 1c (Low Concentration) Working Solution
52 μM Azine Enhancer 1c
263 μM luminol
350 μM hydrogen peroxide Working Solutions of Azine Enhancer 1b (a non-water soluble azine), Phenolic Enhancer 3, Azine Enhancer 1b +Phenolic Enhancer 3 were prepared in 50 mM Tris buffer, pH 8.5 as generally described with respect to Enhancer 1c (Low Concentration) Working Solution. The chemiluminescent enhancers in these comparative solutions (1b and 3) are disclosed in U.S. Pat. No. 5,171,668. The compositions of these comparative working solution solutions are as follows:

Azine Enhancer 1b Working Solution

52 μM Azine Enhancer 1b
263 μM Luminol
350 μM Hydrogen Peroxide

Phenolic Enhancer 3 Working Solution 13.5 μM Phenolic Enhancer 3
263 μM Luminol
350 μM Hydrogen Peroxide Azine Enhancers 1b +Phenolic Enhancer 3 Working Solution 52 μM Azine Enhancer 1b
13.5 μM Phenolic Enhancer 3
263 μM Luminol
350 μM Hydrogen Peroxide The working solutions were added to the membrane strips and incubated for five minutes before being placed between clear plastic sheets. The membrane strips were exposed to film for 1 minute followed by additional reexposures for 1 minute, after 5 minutes, 30 minutes, 1 hour, 2 hours and 24 hours. The relative intensities of the luminescence at the various SA-HRP concentrations after the 30 minute reexposure is described in Table 10. Table 11 presents the relative intensities of the different working solutions at 20 pg of the SA-HRP after the various times of reexposure.

TABLE 10

Blot Application

|  | Relative Intensity 20 pg SA-HRP | Relative Intensity 5 pg SA-HRP | Relative Intensity 2 pg SA-HRP |
|---|---|---|---|
| Working Solution of the Present Invention 1.5 mM Azine Enhancer 1c | 4,043,904 | 2,362,128 | 1,760,152 |
| Azine Enhancer 1c (Low Concentration) 52 μM Azine Enhancer 1c | 859,624 | 504,528 | 93,200 |
| Azine Enhancer 1b 52 μM Azine Enhancer 1b | 573,864 | 0 | 0 |
| Phenolic Enhancer 3 13.5 μM Enhancer 3 | 598,072 | 106,776 | 0 |
| Azine Enhancer 1b + Phenolic 3 52 μM Azine Enhancer 1b + 13.5 μM Phenolic Enhancer 3 | 552,560 | 0 | 0 |

TABLE 11

Blot Application Over Time

|  | Relative Intensity 1 minute | Relative Intensity 5 minutes | Relative Intensity 30 minutes | Relative Intensity 1 hours | Relative Intensity 2 hours | Relative Intensity 24 hours |
|---|---|---|---|---|---|---|
| Working Solution of the Present Invention 1.5 mM Azine Enhancer 1c | 4,568,920 | 4,222,800 | 4,043,904 | 4,517,952 | 3,334,728 | 841,136 |
| Azine Enhancer 1c (Low Concentration) 52 μM Azine Enhancer 1c | 848,784 | 867,184 | 859,624 | 921,768 | 822,856 | 409,704 |
| Azine Enhancer 1b 52 μM Azine Enhancer 1b | 457,800 | 628,408 | 573,864 | 502,376 | 418.984 | 0 |
| Phenolic Enhancer 3 13.5 μM Enhancer 3 | 747,888 | 707,432 | 598,082 | 492,016 | 274,888 | 0 |
| Azine Enhancer 1b + Phenolic Enhancer 3 52 μM Azine Enhancer 1b + 13.5 μM Phenolic Enhancer 3 | 676,744 | 653,032 | 552,560 | 427,664 | 135,232 | 0 |

The same enhancer working solutions were analyzed in a microtiter plate luminometer based application as described in Example 1. The relative light units of the luminescence at the various B-HRP concentrations after 5 minutes is described in Table 12. Table 13 presents the RLU of the different enhancer working solutions at 25 pg of the B-HRP over a two hour time period.

TABLE 12

Microtiter Plate Application

|  | Relative Intensity 250 pg B-HRP | Relative Intensity 25 pg SA-HRP | Relative Intensity 5 pg SA-HRP |
|---|---|---|---|
| Working Solution of the Present Invention 1.5 mM Azine Enhancer 1c | 848.89 | 50.45 | 3.31 |
| Azine Enhancer 1c (Low Concentration) 52 μM Azine Enhancer 1c | 18.41 | 1.29 | 0.08 |
| Azine Enhancer 1b 52 μM Azine Enhancer 1b | 16.30 | 0.10 | 0 |
| Phenolic Enhancer 3 13.5 μM Enhancer 3 | 0.328 | 0 | 0 |
| Azine Enhancer 1b + Phenolic Enhancer 3 52 μM Azine Enhancer 1b + 13.5 μM Phenolic Enhancer 3 | 10.23 | 0 | 0 |

TABLE 13

Microtiter Plate Application Over Time

|  | RLU 1 minute | RLU 5 minutes | RLU 15 minutes | RLU 30 minutes | RLU 1 hour | RLU 2 hours |
|---|---|---|---|---|---|---|
| Working Solution of the Present Invention 1.5 mM Azine Enhancer 1c | 60.3 | 56.52 | 57.63 | 55.54 | 51.26 | 40.48 |
| Azine Enhancer 1c (Low Concentration) 52 μM Azine Enhancer 1c | 1.79 | 1.59 | 1.40 | 1.24 | 1.37 | 1.01 |
| Azine Enhancer 1b 52 μM Azine Enhancer 1b | 0.06 | 0.13 | 0.32 | 0.76 | 0.65 | 0.04 |
| Phenolic Enhancer 3 13.5 μM Enhancer 3 | 0.001 | 0.002 | 0.001 | 0.002 | 0.002 | 0.002 |

TABLE 13-continued

Microtiter Plate Application Over Time

|  | RLU 1 minute | RLU 5 minutes | RLU 15 minutes | RLU 30 minutes | RLU 1 hour | RLU 2 hours |
|---|---|---|---|---|---|---|
| Azine Enhancer 1b + Phenolic Enhancer 3 | 0.001 | 0.002 | 0.004 | 0.004 | 0.008 | 0.002 |
| 52 μM Azine Enhancer 1b + 13.5 μM Phenolic Enhancer 3 | | | | | | |

The high luminosity and the extended duration thereof exhibited by the working solution of the present invention are evident from Tables 10–13.

EXAMPLE 8
Other Water Soluble Azine Enhancer Comparisons This example illustrates other 10-substituted water soluble phenothiazines and phenoxazines derivatives as azine enhancers.

Dot blotting procedures and a luminometer based microtiter plate procedure as described in Example 1 were performed. Azine Enhancers 1b, 1c, 1d and 1e were analyzed at 50 μM with 1 mM Sodium Luminol in a dot blot application. Azine Enhancers 1b, 1c, 1d, 1e, 1f, 1g, and 1h *were analyzed at* 1.5 mM with 5 mM Sodium Luminol in a dot blot application. Azine Enhancers 1c, 1d, 1f, 1g, 1h, 1i, and 2b were analyzed at 1.5 mM with 5 mM Sodium Luminol in a microtiter plate procedure.

Figure 7:
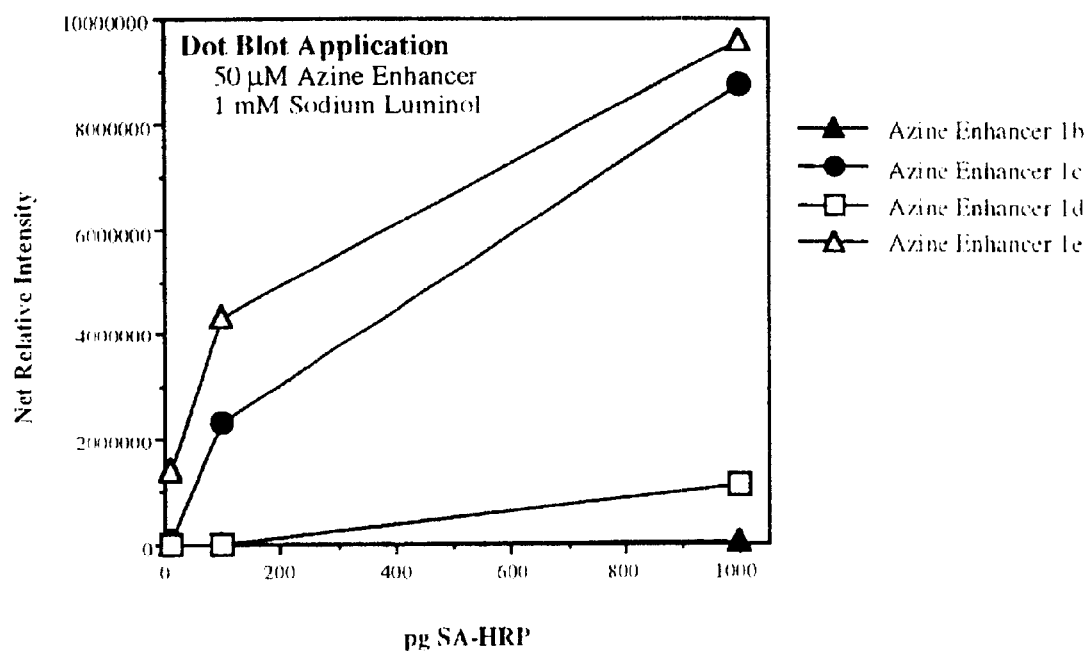
FIG. 7 shows Dot Blot Application results with 4 Enhancers and Luminol at 50 $\mu$M Ehancer with SA-HRP.
Figure 8:
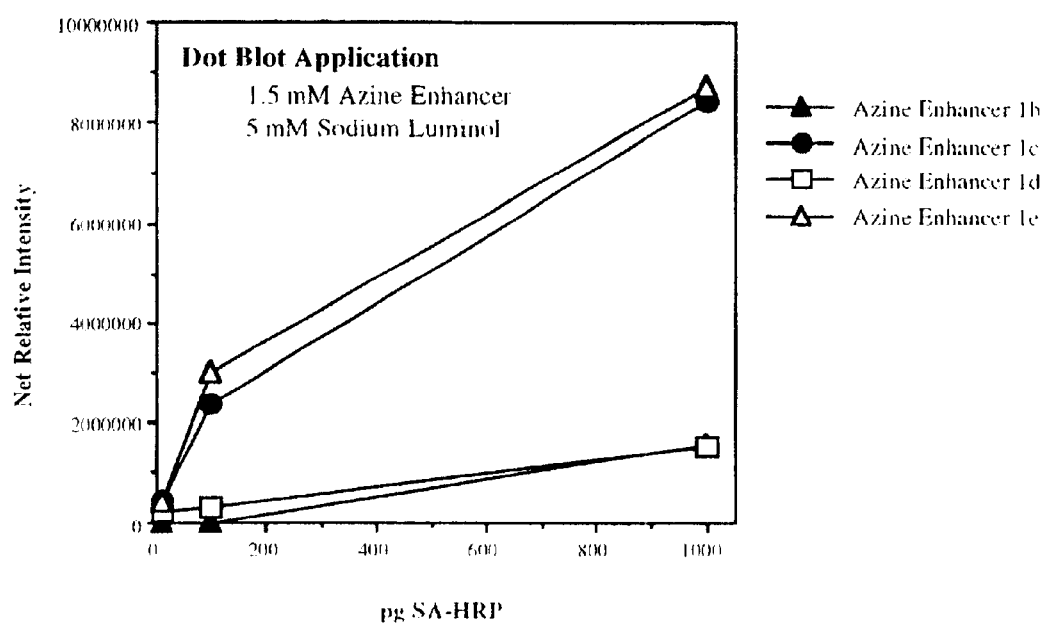
FIG. 8 shows Dot Blot Application results with 4 Enhancers and Luminol at 1.5 mM Enhancer with SA-HRP.
Figure 9:
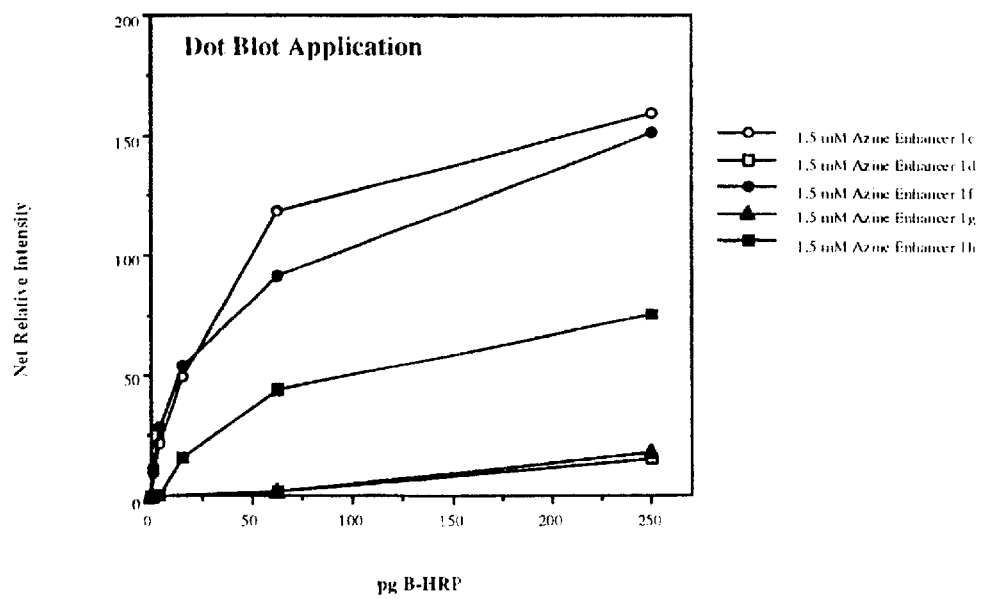
FIG. 9 shows Dot Blot Application results with 5 Enhancers and Luminol at 1.5 mM Enhancer with B-HRP.
Figure 10:
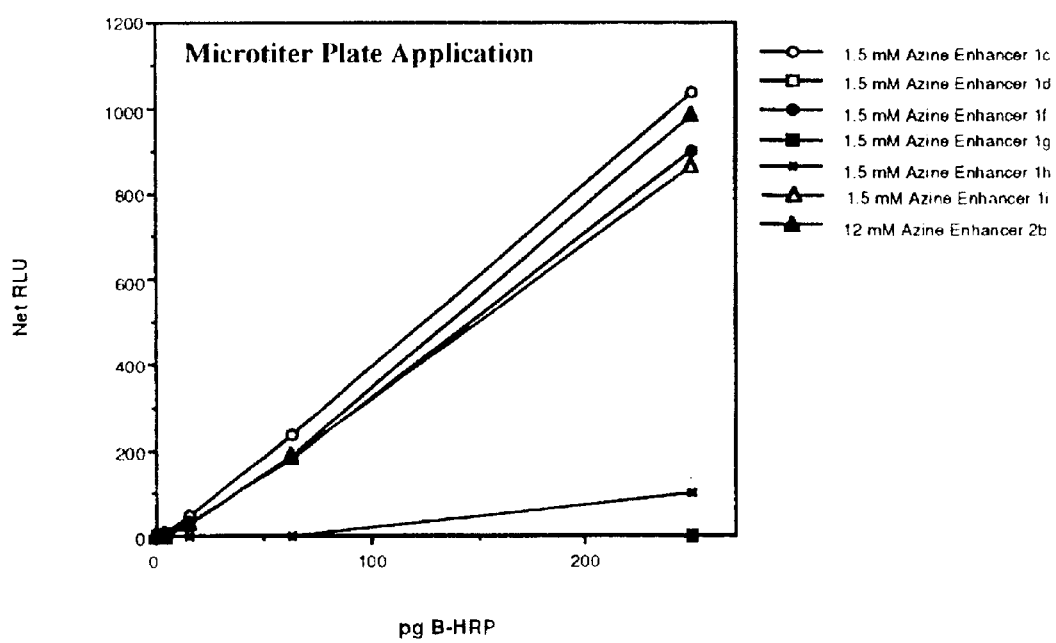
FIG. 10 shows Dot Blot Application results with 7 Enhancers and Luminol with B-HRP.

Table 14 and Table 15 summarizes the luminosity produced by other Azine Enhancers of the present invention at either 50 μM or 1.5 mM in a blotting application. Table 16 summarizes other Azine Enhancers of the present invention at 1.5 mM in a microtiter plate assay. Dose response curvse in dot blot applications are illustrated in FIG. 7 with 50 μM Azine Enhancer and FIGS. 8 and 9 with 1.5 mM Azine Enhancer. FIG. 10 illustrates dose response curves with the Azine Enhancers of the present invention in a microtiter plate assay.

TABLE 14

Blot Application

|  | Net Relative Intensity at 1000 pg SA-HRP | Net Relative Intensity at 100 pg SA-HRP | Net Relative Intensity at 10 pg SA-HRP |
|---|---|---|---|
| 50 μM Azine Enhancer 1b | 25,925 | 0 | 0 |
| 50 μM Azine Enhancer 1c | 8,763,560 | 2,314,240 | 99,400 |
| 50 μM Azine Enhancer 1d | 1,106,656 | 0 | 0 |
| 50 μM Azine Enhancer 1e | 9,599,880 | 4,351,240 | 1,416,056 |
| 1.5 mM Azine Enhancer 1b | 1,571,968 | 0 | 0 |
| 1.5 mM Azine Enhancer 1c | 8,426,960 | 2,356,176 | 423,856 |
| 1.5 mM Azine Enhancer 1d | 1,538,600 | 311,048 | 225,632 |
| 1.5 mM Azine Enhancer 1e | 8,706,320 | 3,021,440 | 432,352 |

TABLE 15

Blot Application

|  | Net Relative Intensity at 250 pg B-HRP | Net Relative Intensity at 62.5 pg B-HRP | Net Relative Intensity at 15.6 pg B-HRP | Net Relative Intensity at 3.9 pg B-HRP | Net Relative Intensity at 0.98 pg B-HRP |
|---|---|---|---|---|---|
| 1.5 mM Azine Enhaneer 1c | 159.64 | 118.41 | 49.21 | 22.32 | 10.02 |
| 1.5 mM Azine Enhaneer 1d | 15.63 | 1.70 | 0 | 0 | 0 |
| 1.5 mM Azine Enhaneer 1f | 151.53 | 91.44 | 54.12 | 28.77 | 12.05 |
| 1.5 mM Azine Enhancer 1g | 17.92 | 2.16 | 0 | 0 | 0 |
| 1.5 mM Azine Enhancer 1h | 75.58 | 44.09 | 16.09 | 0.55 | 0.20 |

TABLE 16

Microtiter Plate Application

|  | Net RLU at 250 pg B-HRP | Net RLU at 62.5 pg B-HRP | Net RLU at 15.6 pg B-HRP | Net RLU at 3.9 pg B-HRP | Net RLU at 0.98 pg B-HRP |
|---|---|---|---|---|---|
| 1.5 mM Azine Enhancer 1c | 1037.00 | 236.10 | 48.60 | 9.80 | 1.90 |
| 1.5 mM Azine Enhancer 1d | 0.19 | 0.00 | 0.00 | 0.00 | 0.00 |
| 1.5 mM Azine Enhancer 1f | 899.10 | 181.00 | 33.80 | 6.50 | 1.30 |
| 1.5 mM Azine Enhancer 1g | 0.35 | 0.00 | 0.00 | 0.00 | 0.00 |
| 1.5 inM Azine Enhancer 1h | 99.20 | 1.50 | 0.19 | 0.17 | 0.08 |
| 1.5 mM Azine Enhancer 1i | 864.65 | 182.48 | 26.08 | 0.74 | 0.05 |
| 12 mM Azine Enhancer 2b | 933.61 | 89.19 | 26.15 | 3.22 | 0.46 |

EXAMPLE 9
Western Blot Application

This example illustrates the present invention with a Western Blotting application in general accordance with the blotting method described by Towbin, H. et al. Proc. Natl. Acad. Sci. 76, 4350–4354 (1979). Various concentrations of human wild-type p53 baculovirus lysate were electrophoretically separated on a 12% SDS polyacrylamide gel (apparatus and gel obtained from Novex) and then transferred to nitrocellulose membrane using standard procedures (apparatus from Bio-Rad). The nonspecific sites were blocked with SuperBlock™ Blocking Buffer containing 0.05% Tween™ -20. Mouse anti-p53 at 0.013 μg/ml was added to the membrane for 1 hour followed a PBS wash to remove unbound antibody. The membrane was then incubated for 1 hour with 20 ng/ml of horseradish peroxidase labeled goat anti-mouse followed by additional washing. The membrane was then cut into two sections.

Figure 11:
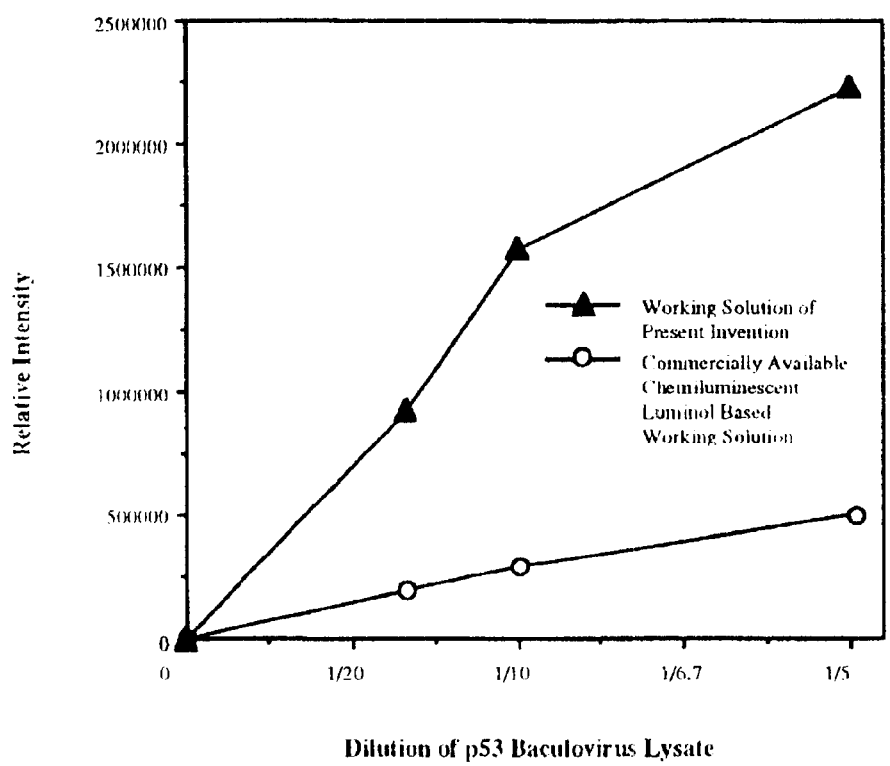
FIG. 11 shows Relative Intensity versus Dilution of p53 Baculovirus Lysate for a Solution of the Present Invention versus a Working Solution of a Commercially Available Luminol-Based Chemiluminescent Solution.

The working solution of the present invention and a commercially available luminol based working solution as described in Example 1 were prepared. The working solutions were added to the membranes and incubated for 5 minutes. The membranes were placed between clear plastic sheets and exposed to X-ray film (DuPont/NEN Reflection™ X-Ray Film) for 30 seconds. The film was developed and subsequently scanned by a reflectance densitometer (Hewlett Packard). The relative intensity for all protein bands was determined using Collage™ Software from Fotodyne. No background signal was detectable. FIG. 11 illustrates the relative intensities obtained using the two working solutions. From FIG. 11, it is evident that, with respect to the described Western Blot assay, the working solution of the present invention exhibits markedly enhanced luminositye and, in turn, increased sensitivity compared to the commercially available luminol based product.

EXAMPLE 10
Southern Blot Application

This example illustrates the present invention in a typical Southern Blot application.

A 1 kilobase DNA (1kb DNA) ladder (Gibco) was separated on a 0.7% agarose 0.5×Tris/Boric Acid/EDTA (TBE) gel (1 ng/lane to 7 pg/lane). The separated DNA was transferred by downward alkaline transfer (Chomczynski, P. Anal. Bioche. 221: 303–305 (1994)) to a positively charged nylon membrane (Biodyne® B) and fixed to the membrane by irradiation in a microwave oven for 2 minutes at 1080 watts.

Prehybridization of the membrane to prevent non-specific binding of a subsequently applied DNA probe was accomplished by incubation in hybridization buffer (10% SDS in 528 mM phosphate, PH 7.2) at 50° C. for 1 hour in a Hybaid® hybridization oven. The probe was prepared by labeling the same 1 kb DNA ladder used for separation with biotin using a Psoralen-biotin labeling kit (Schleicher and Schuell). The probe, in hybridization buffer at a concentration of 5 ng/ml was added to the membrane with the resulting hybridization reaction occurring overnight at 50° C. in the Hybaid® oven.

The membrane was washed with 5×SSC (75 mM sodium chloride, 7.5 mM sodium citrate, pH 7.0) containing 0.5% SDS to remove the unbound DNA probe. The membrane was then incubated with a casein containing blocking buffer to block non-specific protein binding sites. Horseradish peroxidase conjugated streptavidin was then added to the blocking buffer at a concentration of 0.05 μg/ml and incubated for 1 hour.

Figure 12:
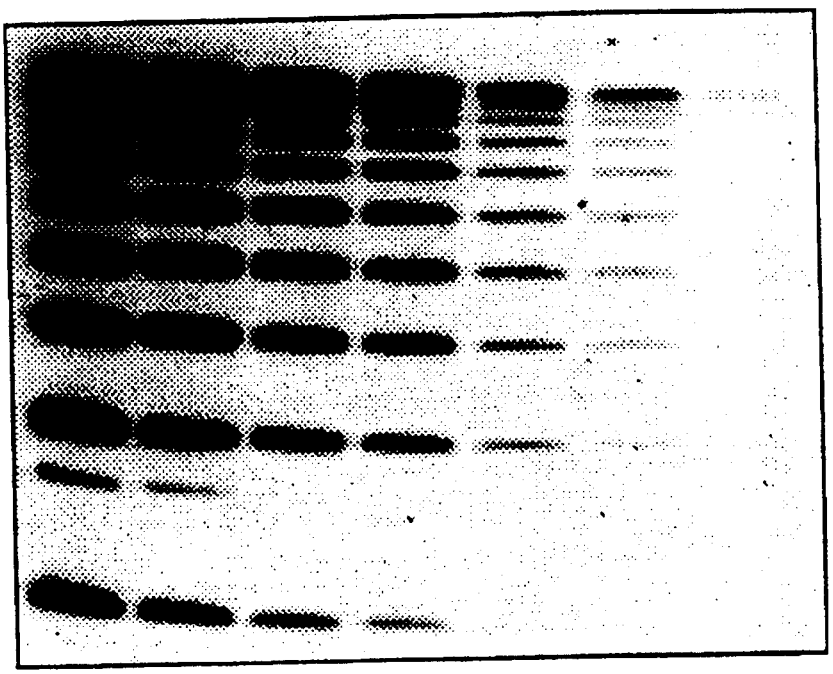
FIG. 12 shows a photographic image of a Southern blot assay using the chemiluminescent working solution of the present invention.

The membrane was washed with tris buffered saline containing 0.5% SDS to remove unbound enzyme conjugate. The working solution of the present invention was prepared as described in Example 1. The membrane was incubated with the working solution for 5 minutes and then exposed to film for 30 minutes. The film was developed and scanned using a BioRad densitometer (FIG. 12). The luminescence developed in this Southern Blot assay is produced quickly, in contrast to conventional 1,2-dioxetane based alkaline phosphatase systems, and continues over an extended period of time, in contrast to commercially available enhanced luminol based horseradish peroxidase systems.

Northern blotting assays for detection of RNA can also be accomplished in a similar manner to that illustrated above with respect to detection of DNA. In Northern Blotting, either a DNA or RNA probe can be used.

EXAMPLE 11
ELISA Application

Figure 13:
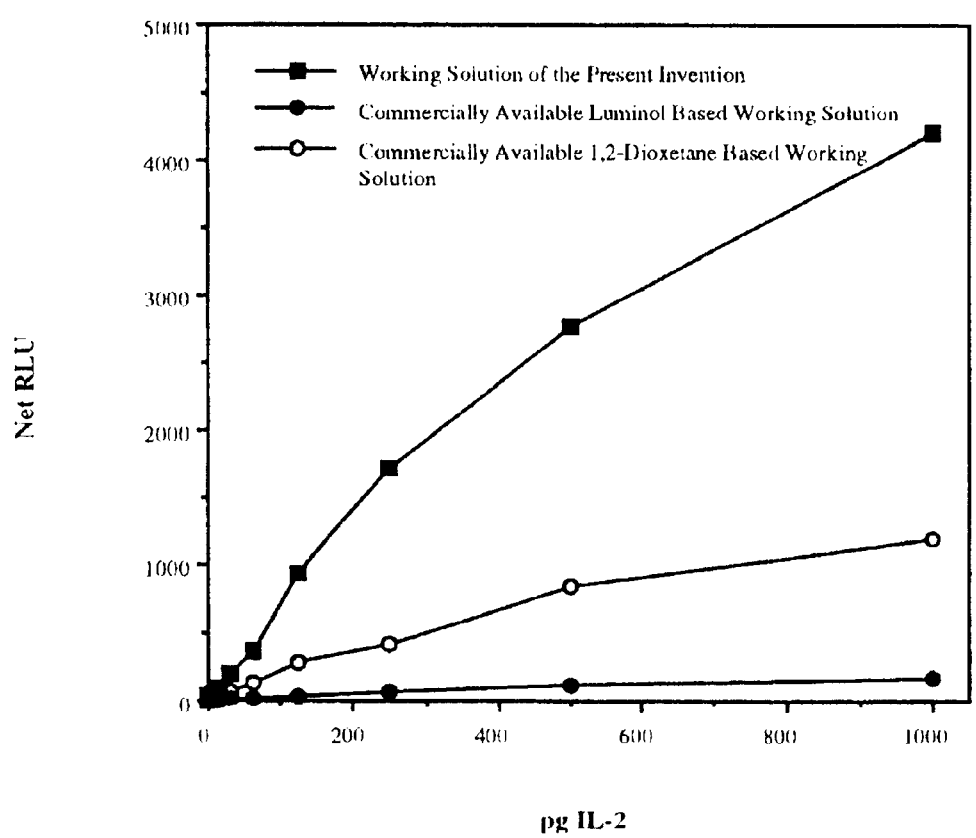
FIG. 13 shows a graphic comparison of Net RLU versus picograms IL-2 for a working solution of the present invention versus two commercially available chemiluminescent working solutions.

The capture antibody, Rat anti-Mouse Interleukin-2 (IL-2) (Pharmingen) was coated on a white microtiter plate overnight at 4° C. The nonspecific sites were blocked with SuperBlock™ Blocking Buffer in PBS. Various concentrations of Recombinant Mouse IL-2 (Pharmingen) were added to the plate and incubated for 2 hours at room temperature. After the plate was washed with PBS/0.05% Tween® -20, Biotinylated Rat anti-Mouse IL-2 (Pharmingen) was added and incubated for 1 hour at room temperature. The plates were washed and then incubated with HRP or Alkaline Phosphatase (AP) labeled NeutrAvidin for 30 minutes followed by several washes. The working solution of the present invention was prepared as described in Example 1 with the addition of 0.4 mM EDTA. Working solutions of a commercially available luminol based system as described in Example 1 and a 1,2-dioxetane based system as described in Example 4. The working solutions were added to the microtiter plate and RLU were determined on a Dynex MLX Microtiter® Luminometer. The plate was read over a 2 hour period of time. The working solution of the present invention and the commercially available luminol based working solution had maximum results within 5 minutes after the addition of the working solution. The 1,2-dioxetane based system required 15 minutes for the signal to reach maximum RLU. FIG. 13 illustrates the dose response of IL-2 for the working solutions.

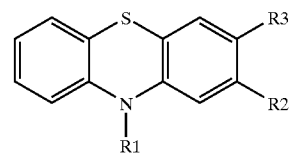

1; General Phenothiazine
1a; R1=H; R2=R3=H (azine poison)
1b; R1=$CH_3$; R2=R3=H
1c; R1=$(CH_2)_3SO_3^-Na^+$; R2=R3=H
1d; R1=$(CH_2)_3N(CH_3)_3+Br^-$; R2=Cl; R3=H
1e; R1=$(CH_2)_3CO_2H$; R2=R3=H
1f; R1=$(CH_2)_4SO_3^-Na^+$; R2=R3=H
1g; R1=$CH_2CH(CH_3)CH_2N(CH_3)_3^+Cl^-$; R2=R3=H
1h; R1=$(CH_2)_4SO_3^-Na^+$; R2=Cl; R3=H
1i; R1=$CH_3$; R2=H; R3=$CH_2O(CH_2)_3SO_3^-Na^+$
1j; R1=R2=R3=H; as the 5oxide/sulfone

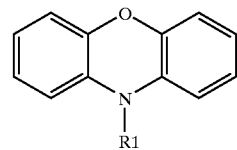

2; General Phenoxazine
2a; R1=H (azine poison)
2b; R1=$(CH_2)_3SO_3^-Na^+$

3; Phenylindophenol/indophenol

What is claimed is:

1. A solution comprising:
   (a) at least one chemiluminescent cyclic diacylhydrazide,
   (b) at least one azine enhancer, and
   (c) at least one oxidizing agent
   wherein for each total mole of said azine enhancer, the solution has less than 0.005 moles of azine compounds having a hydrogen atom bonded to a nitrogen atom of the azine ring.

2. The solution according to claim 1 which is useful for the chemiluminescent assay of peroxidase activity comprising:
   (a) at least one chemiluminescent cyclic diacylhydrazide,
   (b) at least one azine enhancer, and
   (c) at least one oxidizing agent
   wherein for each total mole of said azine enhancer, the solution has less than 0.005 moles of azine compounds having a hydrogen atom bonded to a nitrogen atom of the azine ring.

3. The solution useful for the chemiluminescent assay of peroxidase activity according to claim 2 comprising:
   (a) at least one chemiluminescent cyclic diacylhydrazide,
   (b) at least one azine enhancer, and
   (c) at least one oxidizing agent
   wherein for each total mole of said azine enhancer, the solution has less than 0.001 moles of azine compounds having a hydrogen atom bonded to a nitrogen atom of the azine ring.

4. The solution of claim 2 further comprising at least one chelating agent for divalent metal cations.

5. The solution of claim 4 wherein said chelating agent comprises a polyaminoocarboxylic acid.

6. The solution of claim 1, wherein said oxidizing agent comprises a peroxide or peroxide source.

7. The solution of claim 6, wherein said oxidizing agent comprises a perborate.

8. The solution of claim 6, wherein said azine compounds having a hydrogen atom bonded to a nitrogen atom of the azine ring is present in an amount from 0 to 0.00001 moles per mole of total azine in said solution.

9. The solution of claim 6, wherein said at least one aminoaryl cyclic diacylhydrazide comprises luminol, isoluminol, a substituted derivative of luminol, a substituted derivative of isoluminol, or a salt thereof.

10. The solution of claim 9, wherein said azine compound having a hydrogen atom is present in an amount from 0 to 0.00015 moles per mole of total azine in said solution.

11. The solution according to claim 1, which is useful for the chemiluminescent assay of peroxidase activity comprising:
    (a) at least one chemiluminescent cyclic diacylhydrazide,
    (b) at least one azine enhancer, and
    (c) at least one oxidizing agent
    wherein for each total mole of said azine enhancer, the solution has less than 0.005 moles of poisoning azine compounds having a hydrogen atom bonded to a nitrogen atom of the azine ring, which poisoning compounds reduce the relative luminescence of said solution.

12. The solution useful for the chemiluminescent assay of peroxidase activity according to claim 1 comprising:
    (a) at least one aminoaryl cyclic diacylhydrazide
    (b) at least one azine enhancer, and
    (c) at least one oxidizing agent
    wherein said azine enhancer comprises azine compounds with less than 0.005 moles of poisoning azine compounds for each total mole of azine compounds in said solution.

13. The solution according to claim 1 which is useful for the chemiluminescent assay of peroxidase activity comprising:
    a) at least one chemiluminescent cyclic diacylhydrazide,
    b) at least one azine enhancer, and
    c) at least one oxidizing agent
    wherein for each total mole of said azine enhancer, there is less than 0.005 moles of poisoning azine compounds having a hydrogen atom bonded to a nitrogen atom of the azine ring, which poisoning compounds reduce the relative luminescence of said solution.

14. A solution useful for the chemiluminescent assay of peroxidase activity comprising:
    (a) at least one aminoaryl cyclic diacylhydrazide
    (b) at least one azine enhancer, and
    (c) at least one oxidizing agent
    wherein for each total mole of said azine compounds, the solution has less than 0.005 moles of azine compounds having a hydrogen atom bonded to a nitrogen atom of the azine ring and which azine compounds are capable of reacting with oxidized peroxidase at room temperature, and
    said solution, when placed into contact with a sample comprising peroxidase, will reach a peak chemiluminescent intensity in less than 5 minutes, and chemiluminescence does not diminish in said solution in contact with said sample to less than 75% of said peak luminescence in less than thirty minutes.

15. A solution comprising;
    (a) at least one chemiluminescent cyclic diacylhydrazide in a concentration of 0.5 micromoles to 200 millimoles,
    (b) at least one azine enhancer in a concentration of from 1 micromole to 100 millimoles, and
    (c) at least one oxidizing agent present as from 10 micromoles to 300 millimoles:
    wherein said azine enhancer consists essentially of less than 0.005 moles of azine compounds having a hydrogen atom bonded to a nitrogen atom of the azine ring for each total mole of azine compounds.

16. The solution according to claim 15 which is useful for the chemiluminescent assay of peroxidase activity comprising:
    (a) at least one chemiluminescent cyclic diacylhydrazide,
    (b) at least one azine enhancer, and
    (c) at least one oxidizing agent
    wherein for each total mole of said azine enhancer, the solution has less than 0.005 moles of azine compounds having a hydrogen atom bonded to a nitrogen atom of the azine ring.

17. A solution useful for the chemiluminescent assay of peroxidase activity comprising:
    (a) at least one chemiluminescent cyclic diacylhydrazide in a concentration of 0.5 micromoles to 200 millimoles,
    (b) at least one azine enhancer in a concentration of from 1 micromole to 100 millimoles, and
    (c) at least one oxidizing agent present as from 10 micromoles to 300 wherein said azine enhancer consists essentially of azine compounds with less than 0.005 moles of azine compounds having a hydrogen atom bonded to a nitrogen atom of the azine ring for each mole of azine compound in said solution, and which azine compounds are capable of reacting with oxidized peroxidase at room temperature, and said solution, when placed into contact with a sample comprising peroxidase will reach a peak chemiluminescent intensity in less than 5 minutes, and chemiluminescence does not diminish in said solution in contact with said sample to less than 75% of said peak luminescence in less than thirty minutes.

18. A solution for the chemiluminescent assay of peroxidase activity comprising:
   a) at least one aminoaryl cyclic diacylhydrazide
   b) at least one azine enhancer, and
   c) at least one oxidizing agent
   wherein said azine enhancer comprises azine compounds, and for each total mole of said azine compounds there is less than 0.005 moles of azine compounds in said solution having a hydrogen atom bonded to a nitrogen atom of the azine ring and which azine compounds are capable of reacting with oxidized peroxidase at room temperature, and
   said solution, when placed into contact with a sample comprising peroxidase will reach a peak chemiluminescent intensity in less than 5 minutes, and chemiluminescence does not diminish in said solution in contact with said sample to less than 75% of said peak luminescence in less than thirty minutes.

19. A solution for the chemiluminescent assay of peroxidase activity comprising:
   a) at least one aminoaryl cyclic diacylhydrazide
   b) at least one azine enhancer, and
   c) at least one oxidizing agent
   wherein said azine enhancer comprises for each mole of azine compounds, less than 0.005 moles of poisoning azine compounds.

20. A solution comprising:
   a) at least one chemiluminescent cyclic diacylhydrazide in a concentration of 0.5 micromoles to 200 millimoles,
   b) at least one azine enhancer in a concentration of from 1 micromole to 100 millimoles, and
   c) at least one oxidizing agent in an amount of from 10 micromoles to 300 millimoles,
   wherein said azine enhancer consists essentially of azine compounds with less than 0.005 moles of azine compounds having a hydrogen atom bonded to a nitrogen atom of the azine ring for each mole of azine compound in said solution.

21. The solution according to claim 20 which is useful for the chemiluminescent assay of peroxidase activity comprising:
   a) at least one chemiluminescent cyclic diacylhydrazide,
   b) at least one azine enhancer, and
   c) at least one oxidizing agent
   wherein said azine enhancer consists of azine compounds with less than 0.005 moles of azine compounds having a hydrogen atom bonded to a nitrogen atom of the azine ring for each mole of azine compound in said solution.

22. The solution of claim 20 wherein said oxidizing agent comprises a peroxide or peroxide source.

23. The solution of claim 20 wherein said oxidizing agent comprises a perborate.

24. The solution of claim 23 wherein said azine compound having a hydrogen atom is present in an amount from 0 to 0.0002 moles for each mole of total azine in said solution.

25. The solution of claim 23 wherein said azine compound having a hydrogen atom is present in an amount from 0 to 0.00015 parts mole/mole basis of total azine in said solution.

26. The solution of claim 23 wherein said at least one aminoaryl cyclic diacylhydrazide comprises luminol, isoluminol or a salt thereof.

27. The solution of claim 23 wherein said at least one aminoaryl cyclic diacylhydrazide comprises a substituted derivative of luminol, a substituted derivative of isoluminol, or a salt thereof.

28. A solution for the chemiluminescent assay of peroxidase activity comprising:
   a) at least one chemiluminescent cyclic diacylhydrazide in a concentration of 0.5 micromoles to 200 millimoles,
   b) at least one azine enhancer in a concentration of from 1 micromole to 100 millimoles, and
   c) at least one oxidizing agent present as from 10 micromoles to 300 millimoles,
   wherein said azine enhancer consists essentially of azine compounds with less than 0.005 moles of azine compounds having a hydrogen atom bonded to a nitrogen atom of the azine ring for each mole of azine compound in said solution and which azine compounds are capable of reacting with oxidized peroxidase at room temperature, and
   said solution, when placed into contact with a sample comprising peroxidase will reach a peak chemiluminescent intensity in less than 5 minutes, and chemiluminescence does not diminish in said solution in contact with said sample to less than 75% of said peak luminescence in less than thirty minutes.

* * * * *